United States Patent
Aoki et al.

(10) Patent No.: US 7,809,113 B2
(45) Date of Patent: Oct. 5, 2010

(54) X-RAY SOURCE AND FLUORESCENT X-RAY ANALYZING APPARATUS

(75) Inventors: Nobutada Aoki, Otawara (JP); Akiko Kakutani, Yokohama (JP)

(73) Assignee: Toshiba Electron Tubes & Devices Co., Ltd., Tochigi-Ken (JP)

( * ) Notice: Subject to any disclaimer, the term of this patent is extended or adjusted under 35 U.S.C. 154(b) by 0 days.

(21) Appl. No.: 11/905,911

(22) Filed: Oct. 5, 2007

(65) Prior Publication Data

US 2008/0084966 A1 Apr. 10, 2008

Related U.S. Application Data

(63) Continuation of application No. PCT/JP2007/051710, filed on Feb. 1, 2007.

(30) Foreign Application Priority Data

Feb. 1, 2006 (JP) ............... 2006-024071
Feb. 1, 2006 (JP) ............... 2006-024261

(51) Int. Cl.
*H01J 35/08* (2006.01)
(52) U.S. Cl. .............. 378/124; 378/140; 378/143
(58) Field of Classification Search ........... 378/124, 378/143
See application file for complete search history.

(56) References Cited

U.S. PATENT DOCUMENTS

| 3,229,089 | A | * | 1/1966 | Sasao ............... 378/98.9 |
| 3,963,922 | A | * | 6/1976 | Zulliger et al. ........... 378/45 |
| 4,048,496 | A | * | 9/1977 | Albert ............... 378/45 |
| 4,903,287 | A | * | 2/1990 | Harding ............... 378/119 |
| 5,157,704 | A | * | 10/1992 | Harding ............... 378/119 |
| 6,141,400 | A | * | 10/2000 | Schardt et al. ........... 378/124 |
| 2004/0218725 | A1 | * | 11/2004 | Radley et al. ........... 378/141 |
| 2005/0226378 | A1 | * | 10/2005 | Cocks et al. ........... 378/65 |

FOREIGN PATENT DOCUMENTS

CN 1190662 C 2/2005

(Continued)

OTHER PUBLICATIONS

International Search Report dated May 1, 2007 for PCT/JP 2007/051710.
Chinese Office Action dated Sep. 18, 2009 for Appln. No. 200780000164.2.
Izumi Nakai ed., "Practical Applications of Fluorescent X-ray Analysis", Published by Asakura Shoten, Oct. 20, 2005.

(Continued)

*Primary Examiner*—Hoon Song
*Assistant Examiner*—Mona M Sanei
(74) *Attorney, Agent, or Firm*—Pillsbury Winthrop Shaw Pittman, LLP

(57) ABSTRACT

The present invention relates to an X-ray source for emitting a characteristic X-ray and a fluorescent X-ray analyzing apparatus using the X-ray source. A secondary target is arranged in superposition on a primary target. An electron beam generated by an electron gun enters the primary target, which passes and emits a continuous X-ray. The secondary target transmits and emits a characteristic X-ray excited by the continuous X-ray emitted from the primary target. The primary target and the secondary target are superposed one on the other, so that the continuous X-ray emitted from the primary target efficiently excites the secondary target thereby to efficiently generate the characteristic X-ray.

6 Claims, 18 Drawing Sheets

FOREIGN PATENT DOCUMENTS

| | | |
|---|---|---|
| JP | 2001-008925 | 1/2001 |
| JP | 2001-155670 | 6/2001 |
| JP | 2004-28845 | 1/2004 |

OTHER PUBLICATIONS

Izumi. Nakai, "Present Situation and Outlook of Fluorescent X-Ray Analysis"; Applied Physics, Vo. 74, No. 4, 2005, pp. 455-456.

* cited by examiner

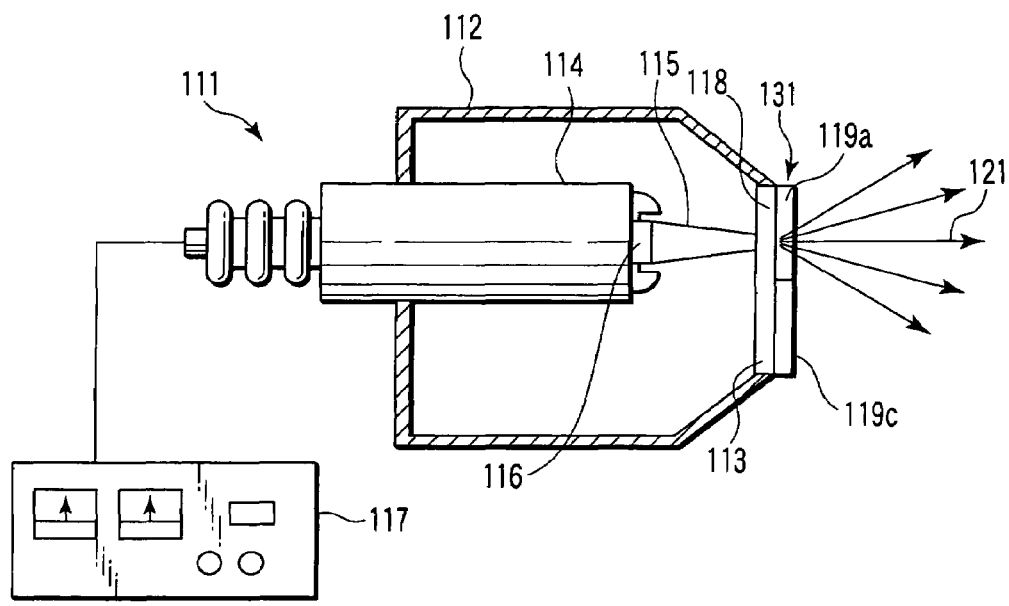
F I G. 10A
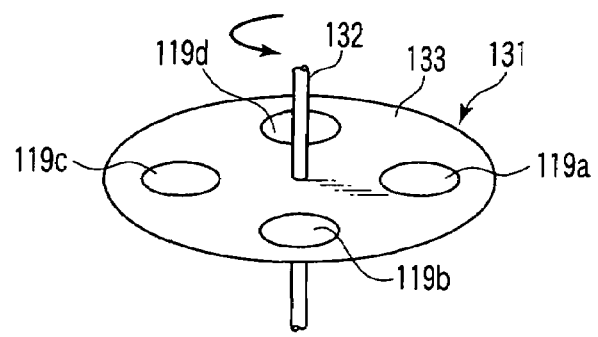
F I G. 10B

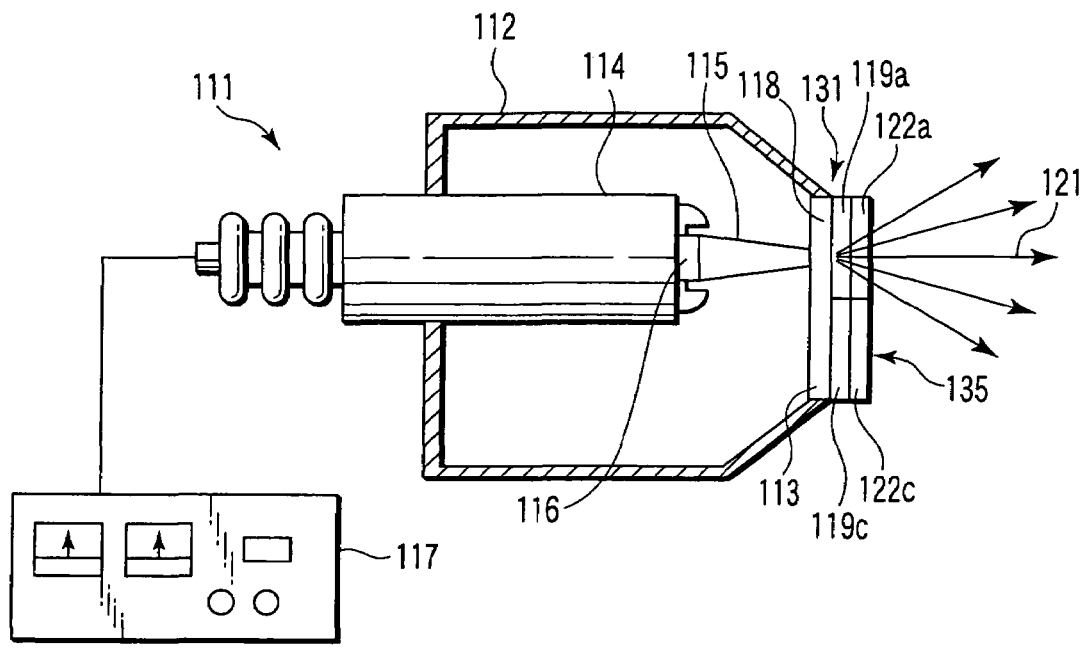
F I G. 11A
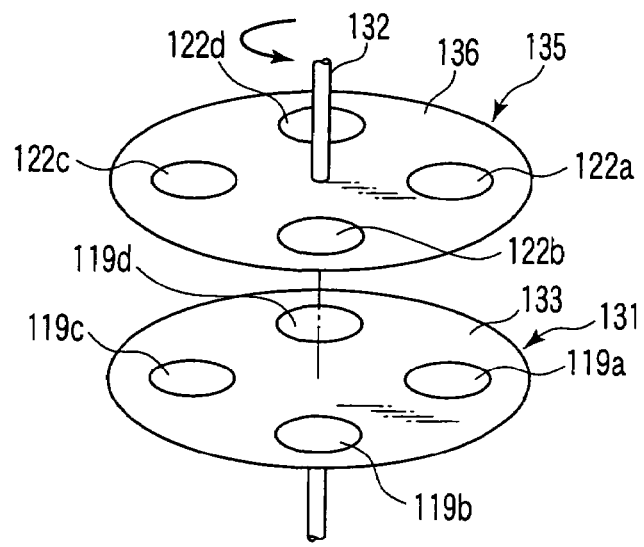
F I G. 11B

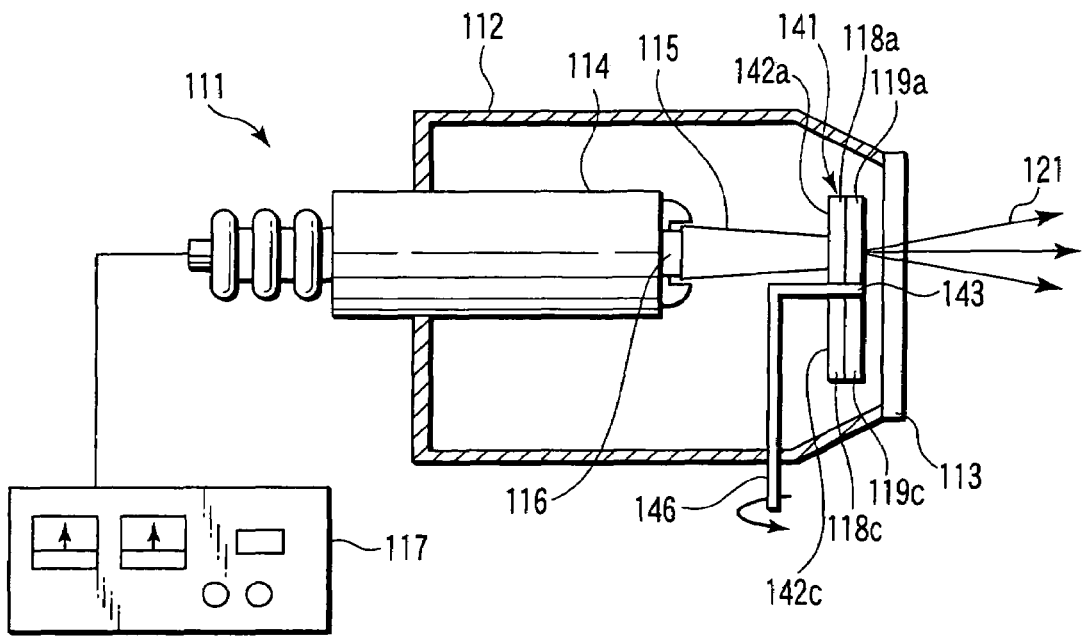
F I G. 12A
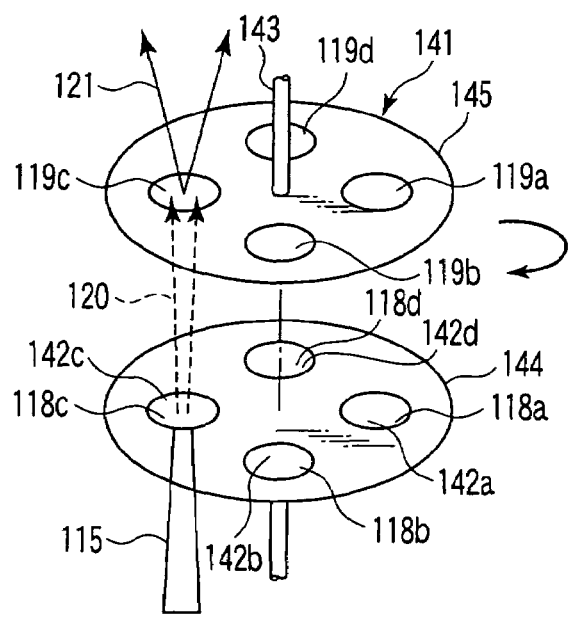
F I G. 12B

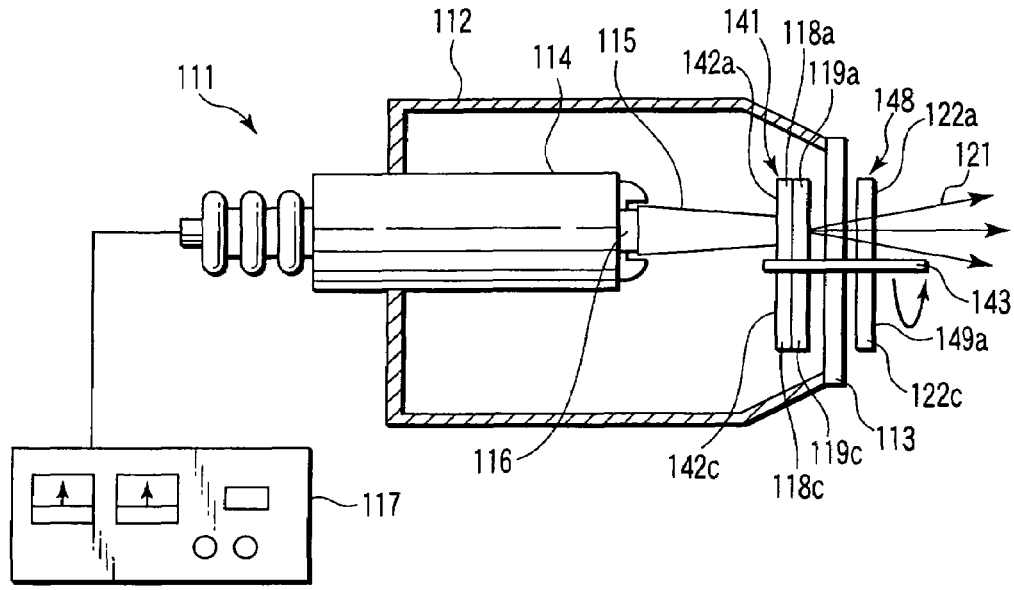
F I G. 13
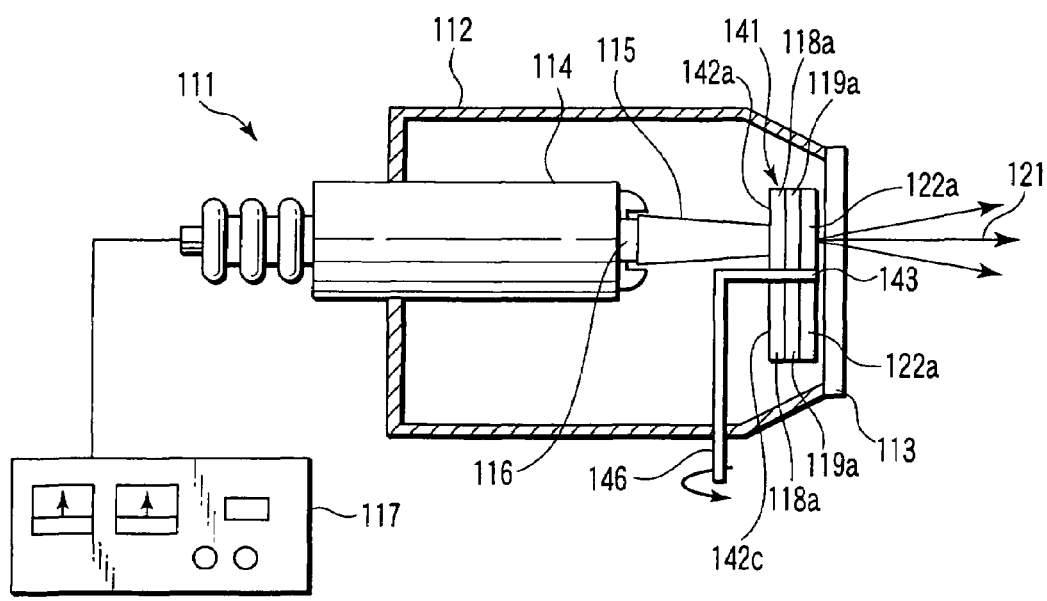
F I G. 14

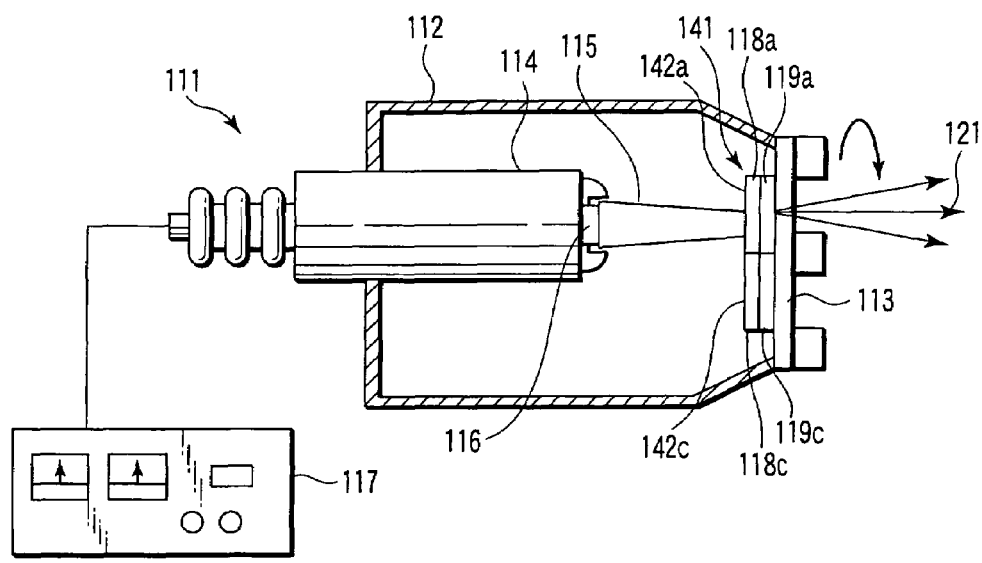
F I G. 15
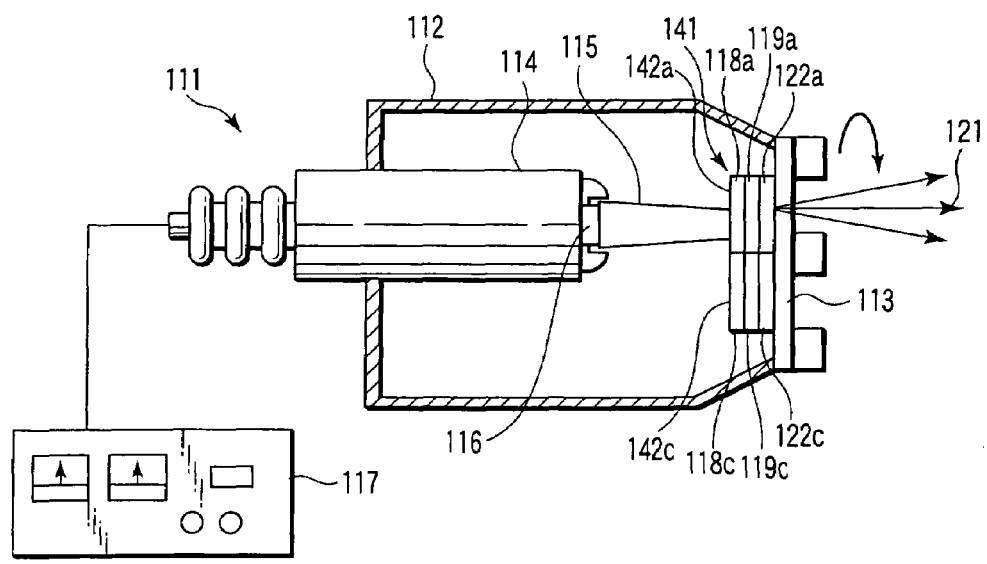
F I G. 16

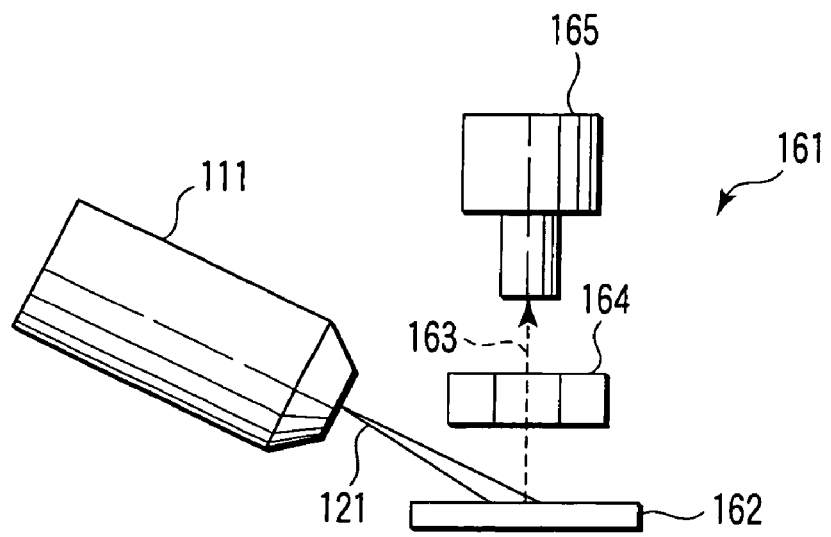
F I G. 17
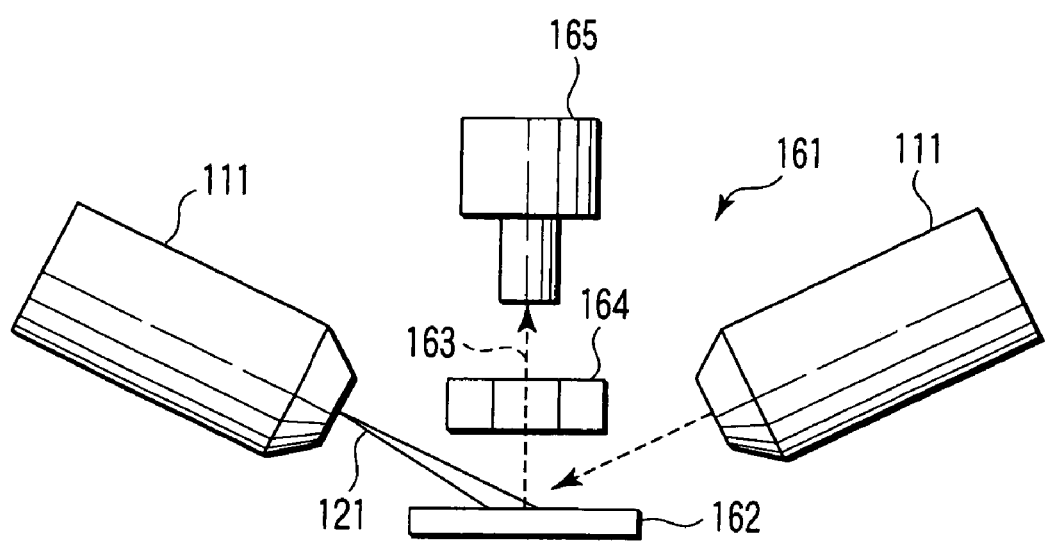
F I G. 18

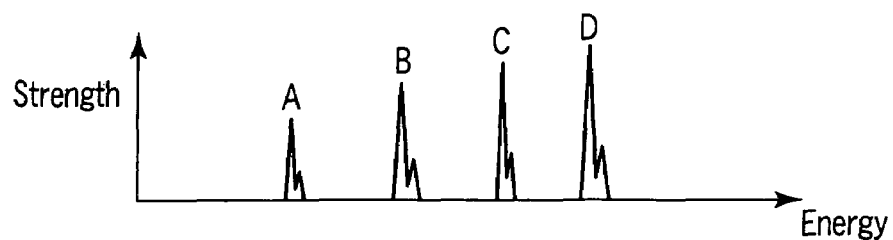
F I G. 23A
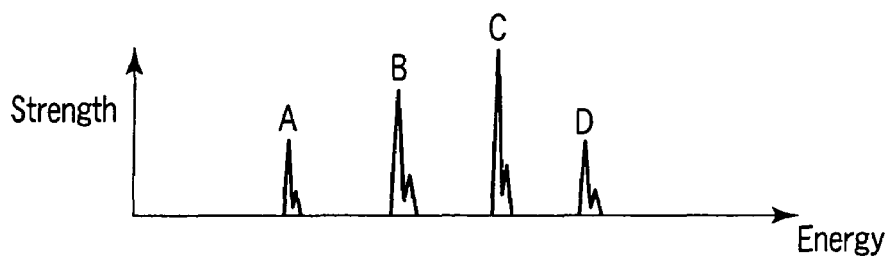
F I G. 23B
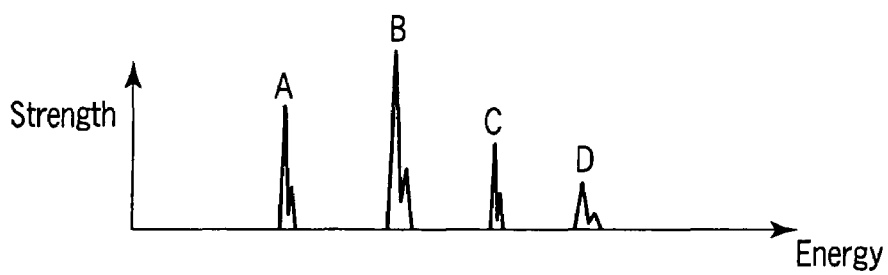
F I G. 23C
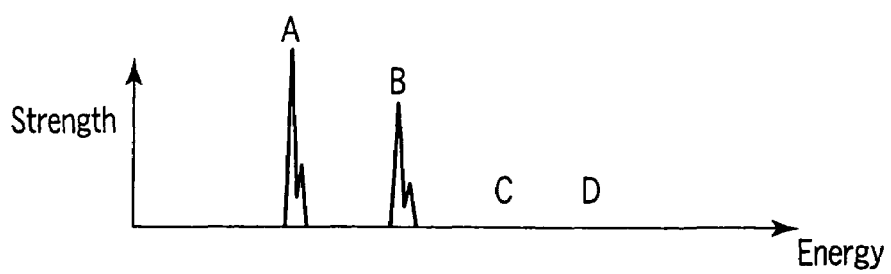
F I G. 23D

X-RAY SOURCE AND FLUORESCENT X-RAY ANALYZING APPARATUS

CROSS REFERENCE TO RELATED APPLICATIONS

This is a Continuation Application of PCT Application No. PCT/JP2007/051710, filed Feb. 1, 2007, which was published under PCT Article 21 (2) in Japanese.

This application is based upon and claims the benefit of priority from prior Japanese Patent Applications No. 2006-024071, filed Feb. 1, 2006; and No. 2006-024261, filed Feb. 1, 2006, the entire contents of both of which are incorporated herein by reference.

BACKGROUND OF THE INVENTION

1. Field of the Invention

The present invention relates to an X-ray source for emitting a characteristic X-ray and a fluorescent X-ray analyzing apparatus using the X-ray source.

2. Description of the Related Art

In an ordinary X-ray source, electrons accelerated at a high voltage enter an anode constituting a target thereby to emit the bremsstrahlung X-ray and the characteristic X-ray unique to the target (see, for example, Jpn. Pat. Appln. KOKAI Publication No. 2004-28845, pp. 4-5, FIGS. 1 and 2).

The bremsstrahlung X-ray is a continuous energy spectrum configured of white and has a spectral distribution changing with the incident electron energy. The characteristic X-ray, on the other hand, not dependent on the electron energy, is monochromatic and has a single energy distribution unique to the target. In fluorescent X-ray analysis, the energy distribution of the signal of the fluorescent X-ray emitted at the time of incidence of the characteristic X-ray into the specimen is measured to identify the type and amount of the elements in the specimen. For this purpose, various X-ray sources devised to improve the analysis performance are used.

In the fluorescent X-ray analyzing apparatus, the specimen is excited using the characteristic X-rays having a known spectrum. In this way, the signal of the fluorescent X-ray and the noise component constituting the scattering of the incident X-ray are easily distinguished from each other, which enables element analysis at a high S/N ratio. In view of this, attempts have been made at practical application of an X-ray source that emits an almost monochromatic X-ray spectrum.

FIG. 29 shows an example of a general configuration of a high resolution fluorescent X-ray analyzing apparatus using the characteristic X-ray described above. In this case, an ordinary X-ray source 1 is used, and a continuous X-ray 2 constituting the primary X-ray of the continuous energy spectrum emitted from the particular X-ray source 1 is applied to a secondary target 3. Thus, a characteristic X-ray 4 is emitted and irradiated on a specimen 6 through a collimator 5 arranged externally, so that a fluorescent X-ray 7 emitted upon excitation of the elements on the surface of the specimen 6 is detected by an X-ray detector 8.

In the emission system of the characteristic X-ray 4 having this configuration, the X-ray source 1 and the secondary target 3 are required to be arranged in spatial relation to each other. The continuous X-ray 2 is emitted in the entire peripheral direction of 4π, the strength of which reduces in inverse proportion to the square of the distance. In the conventional configuration, therefore, the efficiency of irradiating the secondary target 3 with the continuous X-ray 2 emitted from the X-ray source 1 is low. To increase the strength of the characteristic X-ray 4 emitted from the secondary target 3, therefore, the provision of a large-output X-ray source 1 is required. This increases the size of the high-resolution fluorescent X-ray analyzing apparatus, the power consumption and the X-ray shield scale, resulting in an increased cost which restrains the spread of the use thereof (see, for example, "Present Situation and Outlook of Fluorescent X-Ray Analysis" by Izumi Nakai, Applied Physics, Vol. 74, No. 4, 2005, pp. 455-456).

Also, FIG. 30 shows the total reflection X-ray fluorescence analysis (TXRF) now widely used for inspection of the surface contamination of a semiconductor wafer serving as the specimen 6. The characteristic X-ray 4 is required to enter the semiconductor wafer surface at a very small angle of not larger than 0.1° as consistently as possible, and is suitably, therefore, a sheet beam, for example, including a sectorial fan beam.

BRIEF SUMMARY OF THE INVENTION

In the high-resolution fluorescent X-ray analyzing apparatus described above, the most crucial problem is how to provide an X-ray source 1 that is capable of efficiently generating a characteristic X-ray 4. The configuration using the secondary target 3 is an effective method of emitting the characteristic X-ray 4 while maintaining a high monochromaticity and suppressing the intrusion of the unwanted components (noise) at a low rate. In the conventional method, however, the secondary target 3 is arranged outside the X-ray source 1 and the continuous X-ray 2 is emitted in all the directions (directions of 4π). Therefore, the continuous X-ray 2 is attenuated at the rate of the square of the distance, thereby reducing the availability of the continuous X-ray 2 for exciting the secondary target 3. Further, in view of the need of the space for arranging the secondary target 3 and the monochromatic filter outside the X-ray source 1, the problem is posed that the system becomes bulky.

As a subsidiary effect of this problem, a long distance is required to be set from the secondary target 3 to the specimen 6. In order to ensure the characteristic X-ray 4 irradiated on the specimen 6 is of sufficient strength, therefore, the X-ray source 1 must be of high strength, which contributes to an increased X-ray shield scale and an increased apparatus cost.

Another problem is how to provide an X-ray source which eliminates the unwanted noise components from the X-ray spectrum emission as far as possible and permits the selection of a plurality of characteristic X-rays in accordance with the specimen to be analyzed.

Especially, an X-ray source is required which can produce a low-noise, i.e. high-monochromaticity sheet-like X-ray beam necessary for the high-resolution total reflection X-ray fluorescence analysis very widely used in the semiconductor field.

The present invention has been achieved in view of the aforementioned points, and the object thereof is to provide an X-ray source and a fluorescent X-ray analyzing apparatus using the X-ray source in which the characteristic X-ray can be efficiently generated, the intrusion of the noise components into the characteristic X-ray emitted can be suppressed and the characteristic X-ray in the form of a sheet beam suitable for total reflection X-ray fluorescence analysis, for example, can be easily obtained.

An X-ray source of the present invention comprises: an electron gun which generates an electron beam; a primary target entered by the electron beam from the electron gun to transmit and emit an X-ray; and a secondary target arranged in superposed relation with the primary target to transmit and emit a characteristic X-ray excited by the X-ray emitted from the primary target.

Also, an X-ray source of the present invention comprises: a vacuum container having an X-ray transmission window; an electron gun which generates an electron beam in the vacuum container; a primary target arranged in the vacuum container and entered by the electron beam from the electron gun to emit an X-ray in a direction of reflection; and a secondary target arranged in opposed relation to the primary target around the primary target in the vacuum container, in which a characteristic X-ray excited by the X-ray emitted from the primary target is emitted in the direction of reflection toward the X-ray transmission window.

Also, an X-ray source of the present invention comprises: a vacuum container having an X-ray transmission window; an electron gun which generates an annular electron beam in the vacuum container; a primary target arranged in an annular form in the vacuum container and entered by the annular electron beam from the electron gun to emit an X-ray in a direction of reflection; and a secondary target arranged in opposed relation to the primary target at a center of the primary target in the vacuum container, in which a characteristic X-ray excited by the X-ray emitted from the primary target is emitted in the direction of reflection toward the X-ray transmission window.

Also, an X-ray source of the present invention comprises: a vacuum container having an X-ray transmission window; an electron gun at a ground potential arranged in the vacuum container to generate an electron beam; a primary target arranged in the vacuum container and entered by the electron beam from the electron gun to emit an X-ray in a direction of reflection; and a secondary target arranged at a position of the X-ray transmission window in the vacuum container to transmit and emit a characteristic X-ray excited by the X-ray emitted from the primary target.

Also, an X-ray source of the present invention comprises: an electron gun which generates an electron beam; a primary target entered by the electron beam from the electron gun to transmit and emit an X-ray; and a secondary target unit having a plurality of secondary targets arranged in superposed relation with the primary target and movable with respect to a position of X-ray generation of the primary target, wherein the secondary targets arranged at the position of X-ray generation transmit and emit a characteristic X-ray excited by the x-ray emitted from the primary target.

BRIEF DESCRIPTION OF THE SEVERAL VIEWS OF THE DRAWING

FIG. 10A is a diagram for explaining an X-ray source according to an eighth embodiment of the invention.

FIG. 10B is a perspective view showing a secondary target unit according to the eighth embodiment of the invention.

FIG. 11A is a diagram for explaining an X-ray source according to a ninth embodiment of the invention.

FIG. 11B is a perspective view showing a secondary target unit and a filter unit according to the ninth embodiment of the invention.

FIG. 12A is a diagram for explaining an X-ray source according to a tenth embodiment of the invention.

FIG. 12B is a diagram for explaining the X-ray source according to the tenth embodiment of the invention.

FIG. 13 is a diagram for explaining an X-ray source according to an eleventh embodiment of the invention.

FIG. 14 is a diagram for explaining an X-ray source according to a twelfth embodiment of the invention.

FIG. 15 is a diagram for explaining an X-ray source according to a thirteenth embodiment of the invention.

FIG. 16 is a diagram for explaining an X-ray source according to a fourteenth embodiment of the invention.

FIG. 17 is a diagram for explaining a fluorescent X-ray analyzing apparatus using the X-ray source according to the invention.

FIG. 18 is a diagram for explaining another example of the fluorescent X-ray analyzing apparatus according to the invention.

FIG. 23A is a diagram for explaining the relation between the energy and strength of the electron beam according to a seventeenth embodiment of the invention.

FIG. 23B is a diagram for explaining the relation between the energy and strength of the electron beam according to the seventeenth embodiment of the invention.

FIG. 23C is a diagram for explaining the relation between the energy and strength of the electron beam according to the seventeenth embodiment of the invention.

FIG. 23D is a diagram for explaining the relation between the energy and strength of the electron beam according to the seventeenth embodiment of the invention.

DETAILED DESCRIPTION OF THE INVENTION

Embodiments of the invention will be explained below with reference to the drawings.

Figure 1:
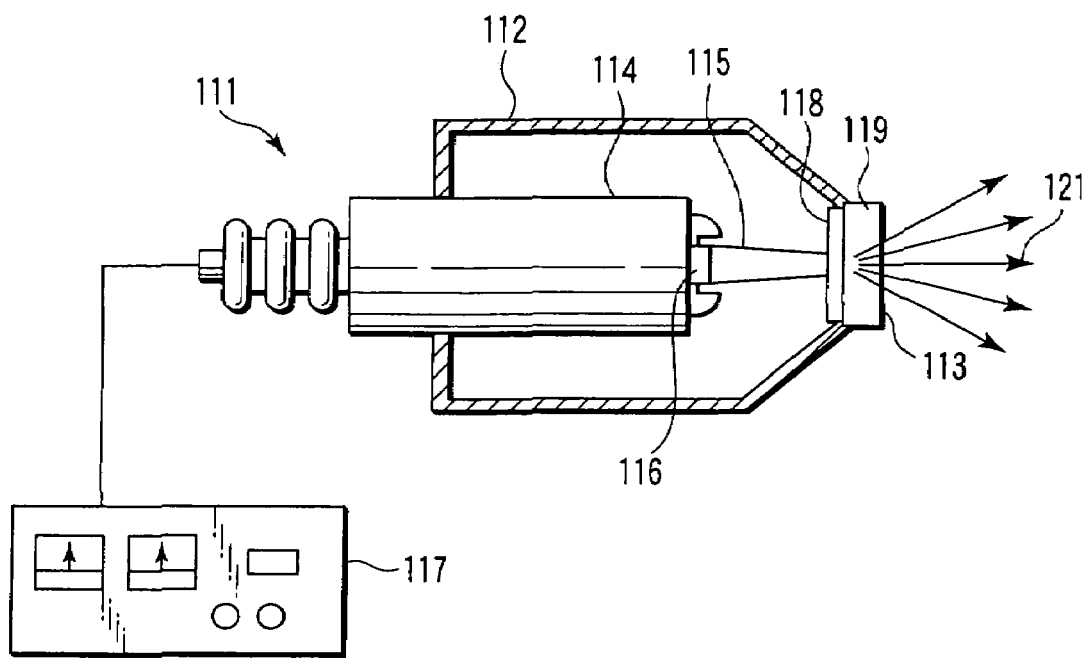
FIG. 1 is a diagram for explaining an X-ray source according to a first embodiment of the invention.
Figure 2:
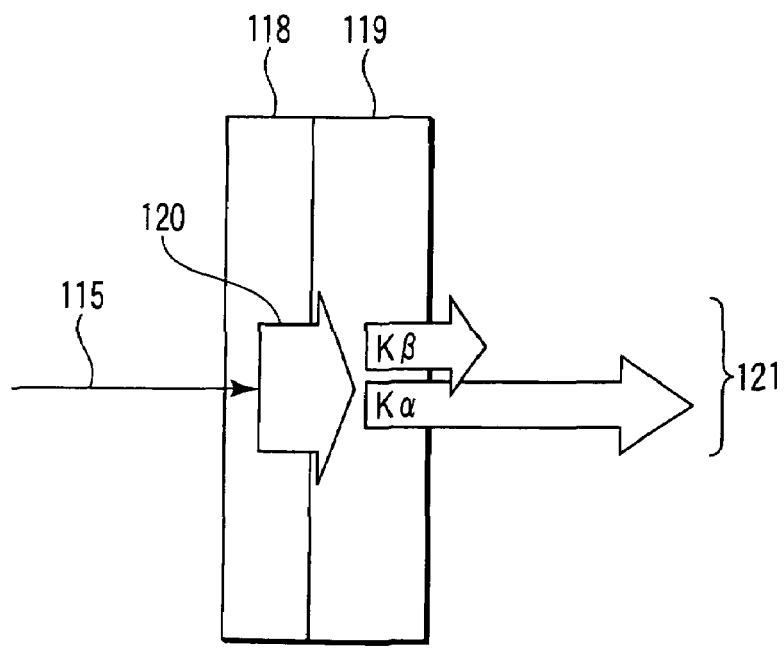
FIG. 2 is a diagram for explaining an X-ray converting operation at the target portion of the same X-ray source.

FIGS. 1 and 2 show an X-ray source according to a first embodiment.

In FIG. 1, an X-ray source 111 has a vacuum container with the interior thereof held in vacuum, and an X-ray transmission window 113 for emitting the X-rays outside is arranged at one end of the vacuum container 112.

An electron gun 114 is arranged at the other end of the vacuum container 112, and an emitter 116 for emitting an electron beam 115 toward the X-ray transmission window 113 is arranged at the end of the electron gun 114 facing the X-ray transmission window 113 in the vacuum container 112. The electron gun 114 generates and accelerates the electron beam 115 through a drive power supply 117.

The X-ray transmission window 113 has arranged therein a primary target 118 facing the electron gun 114 in the vacuum chamber 112, and a secondary target 119 is in closely superposed relation with the outside of the primary target 118.

As shown in FIG. 2, the primary target 118, entered by the electron beam 115, emits a continuous X-ray 120 as the primary X-ray and transmits the continuous X-ray 120 through the secondary target 119. The secondary target 119 emits characteristic X-rays 121 excited by the continuous X-ray 120 emitted through the primary target 118, and transmits and emits the characteristic X-rays 121 out of the vacuum container 112. The characteristic X-rays 121 contain a long-wavelength Kα ray and a short-wavelength Kβ ray as a K ray. The Kα ray and the Kβ ray are contained in the ratio of about 10 to 2.

The electron beam 115 obtained by the drive power supply 117 is assumed to have sufficient energy to excite and emit the characteristic X-rays 121 of the secondary target 119, i.e. the K rays including the Kα ray and the Kβ ray.

Further, in order to effectively emit the characteristic X-rays 121 of the secondary target 119, the primary target 118 of an element having an atomic number larger by about two than the secondary target 119 is most suitably selected as a combination. For example, the primary target 118 of Cu (copper) having the atomic number 29 and the secondary target 119 of Co (cobalt) having the atomic number 27 are selected as a combination.

The continuous X-ray 120 emitted from the primary target 118 is transmitted through the primary target 118 and directly enters the secondary target 119 closely attached to the primary target 118. Unlike in the prior art, therefore, the dispersion of the continuous X-ray 120 with the distance can be minimized, and the continuous X-ray 120 can be efficiently used for excitation of the secondary target 119.

In this way, a compact X-ray source 111 is provided which can efficiently emit the characteristic X-rays 121 having an intended energy.

In view of the fact that the sufficient thickness of the primary target 118 is about equal to the depth of penetration of several μm into the primary target 118 by the energy of incident electrons, the secondary target 119 having the surface thereof coated or plated with the element of the primary target 118 may be used. Thus, the attenuation of the continuous X-ray 120 transmitted through the primary target 118 can be effectively suppressed.

Also, the secondary target 119 which has the function of the X-ray transmission window 113 is required to have a sufficient thickness not to be deformed or destroyed by the pressure difference. In the case where the emission of the low-energy characteristic X-rays 121 is intended, for example, a structure may be employed in which a material such as Be (beryllium) having a small X-ray attenuation rate is used for the X-ray transmission window 113, and the secondary target 119 and the primary target 118 are coated to the required thickness on the particular X-ray transmission window 113.

Further, as an example of the two targets 118, 119 to be selected, stable operation is assured without generating the charge accumulation (charge-up) due to the incidence of the electron beam 115 by using the targets having a combination of the atomic numbers described above in which the primary target 118 is a conductor even in the case where the secondary target 119 is electrically nonconductive or a semiconductor such as Ge (germanium) or Si (silicon).

Figure 3:
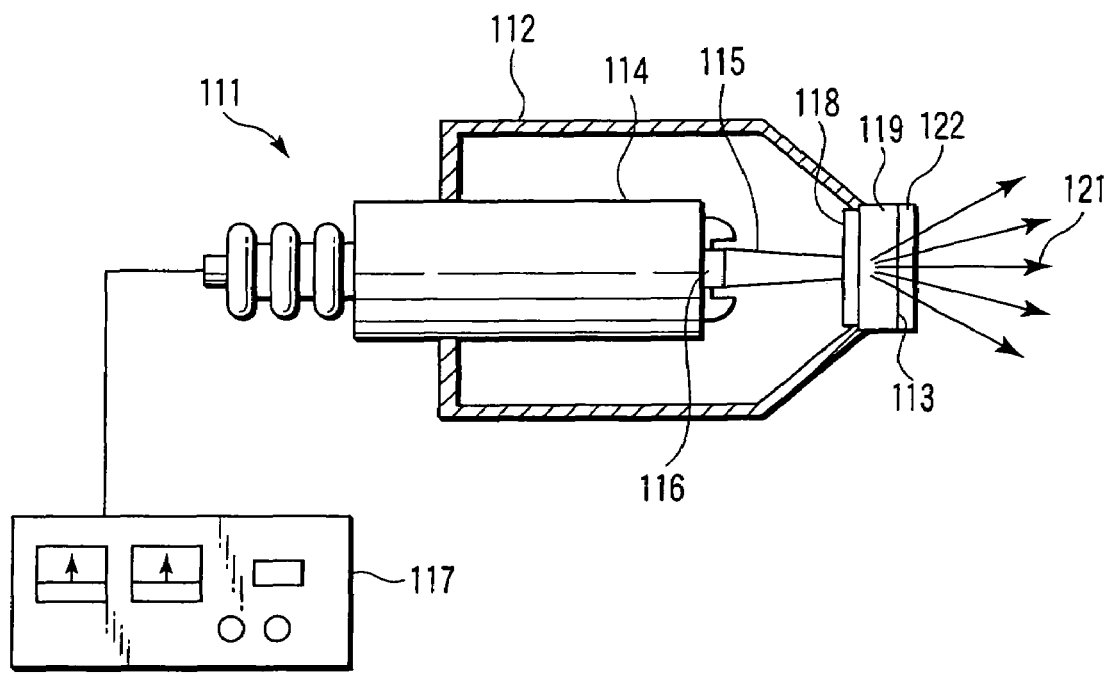
FIG. 3 is a diagram for explaining an X-ray source according to a second embodiment of the invention.
Figure 4:
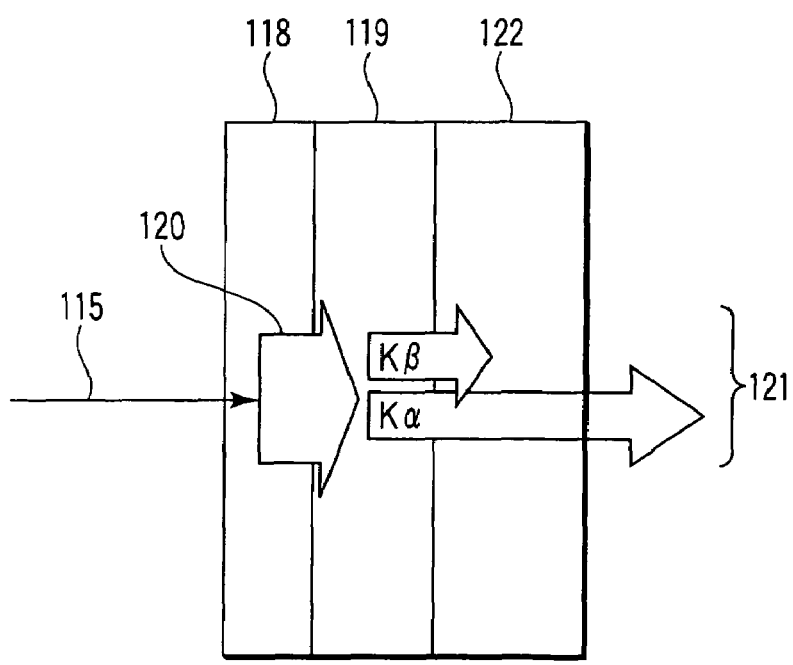
FIG. 4 is a diagram for explaining an X-ray converting operation at the target portion of the same X-ray source.

Next, a second embodiment is shown in FIGS. 3 and 4.

According to this embodiment, the X-ray source 111 of the first embodiment is so configured that a K-edge filter 122, which attenuates the Kβ ray shorter in wavelength than the Kα ray included in the characteristic X-rays 121 of the secondary target 119 and transmits the Kα ray longer in wavelength, is superposed in closely attached relation on the outside of the secondary target 119.

The secondary target 119 and the K-edge filter 122 are required to be selected in an appropriate combination with the element of the K-edge filter 122 suitably having an atomic number smaller by about one than the secondary target 119 for emitting the characteristic X-rays 121. For example, the secondary target 119 of Cu (copper) having the atomic number 29 and the K-edge filter 122 of Ni (nickel) having the atomic number 28 are selected as a combination.

The K-edge filter 122 has a large effect of attenuating the Kβ ray shorter in wavelength than the Kα ray of the characteristic X-rays 121 of the secondary target 119, and transmits the long-wavelength Kα ray. Thus, the long-wavelength Kα ray conspicuously increases in ratio, thereby making it possible to emit the characteristic X-rays 121 high in monochromaticity.

As described above, there is provided a compact X-ray source 111 which emits the characteristic X-rays 121 from the secondary target 119 containing the Kα ray larger in ratio and high in monochromaticity.

Also, according to this embodiment, the thickness of the targets 118, 119 and the K-edge filter 122 is required to be set taking the intended X-ray attenuation rate and the monochromaticity into consideration. In the case where a sufficient thickness of the X-ray transmission window 113 cannot be obtained, however, a material small in X-ray attenuation rate such as Be (beryllium) may be used for the X-ray transmission window 113, on which the targets 118, 119 and the K-edge filter 122 are coated.

Figure 5:
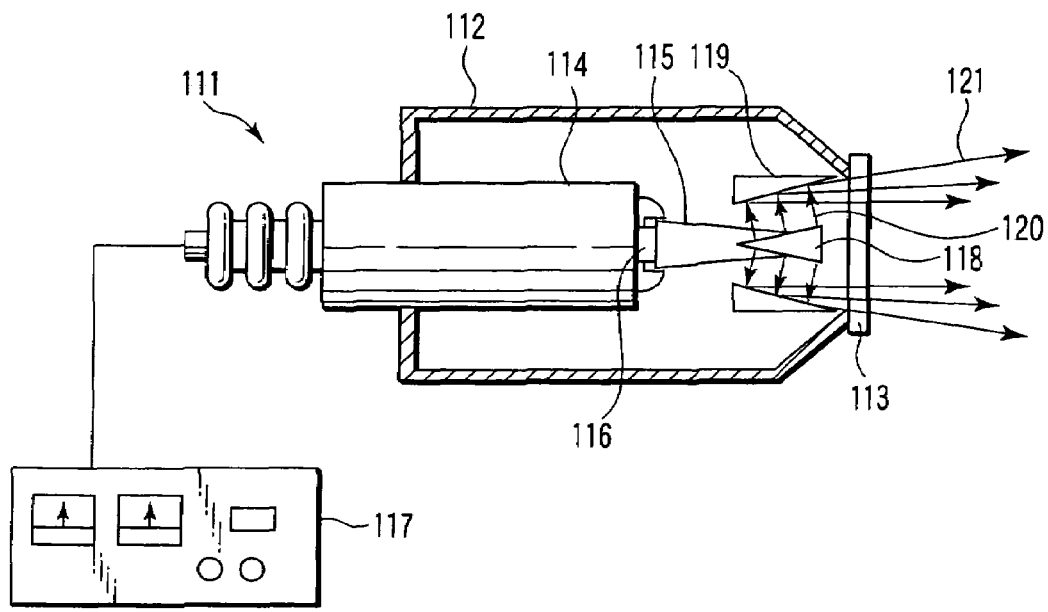
FIG. 5 is a diagram for explaining an X-ray source according to a third embodiment of the invention.

Next, a third embodiment is shown in FIG. 5.

According to this embodiment, like in the first embodiment, the X-ray source 111 is so configured that the primary target 118 entered by the electron beam 115 is in the shape of a cone with the top thereof arranged in opposed relation to the electron gun 114 on the axis of the electron beam 115. Also, the secondary target 119 is in the shape of a cylinder arranged in opposed relation to the periphery of the primary target 118 on a circle concentric with the axis of the electron beam 115, i.e. the center of the primary target 118. The inner peripheral surface of the secondary target 119 is parallel to the surface of the conical primary target 118, for example, and the characteristic X-ray 121 excited by the continuous X-ray 120 incident from the primary target is emitted in the direction of reflection toward the X-ray transmission window 113.

The electron beam 115 generated in the electron gun 114 enters the surface of the conical primary target 118 through the central opening of the secondary target 119, so that the continuous X-ray 120 is emitted in the direction of reflection toward the inner peripheral surface of the secondary target 119 from the surface of the primary target 118. The characteristic X-ray 121 emitted from the primary target 118 enters the inner peripheral surface of the secondary target 119, and is emitted in the direction of reflection toward the X-ray transmission window 113 from the inner peripheral surface of the secondary target 119. The characteristic X-rays 121 are emitted outside from the secondary target 119 through the X-ray transmission window 113.

In this case, the distance between the primary target 118 and the secondary target 119 is longer than in the configuration of the first embodiment, and the efficiency of radiation and excitation of the secondary target 119 is reduced. Nevertheless, the distance between the primary target 118 and the secondary target 119 can be shortened by arranging them in the vacuum container 112. Thus, the continuous X-ray 120 emitted from the primary target 118 can be efficiently utilized for excitation of the secondary target 119, and the characteristic X-rays 121 can be generated efficiently. Further, both the primary target 118 and the secondary target 119 can be formed in bulk structure having a large heat capacity with an arbitrary thickness. Therefore, the resistance to thermal shock is higher than that of the transmission system of the first embodiment. Thus, the incident electron beam current can be set to a large amount and large-output characteristic X-rays 121 can be emitted.

Also, in the case where the incident electron beam current is further increased in amount, the primary target 118, and if required, the second target 119 can be cooled with water for a further improved heat resistance.

As described above, a compact X-ray source 111 is provided in which the endurance of the targets 118, 119 can be secured even against a large current, and which can emit large-output characteristic X-rays 121.

Figure 6:
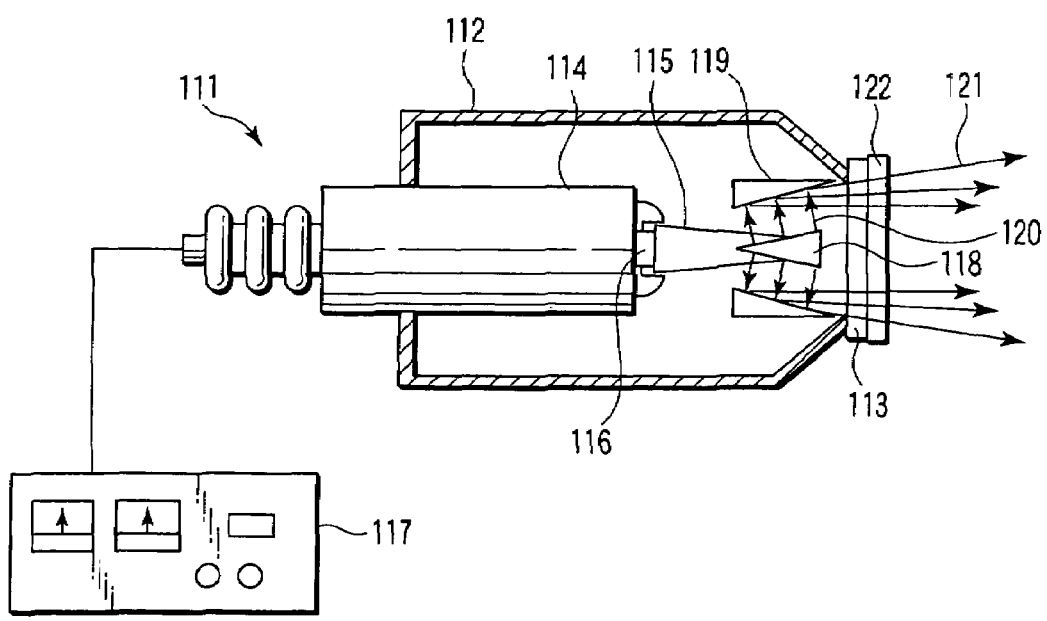
FIG. 6 is a diagram for explaining an X-ray source according to a fourth embodiment of the invention.

Next, a fourth embodiment is shown in FIG. 6.

According to this embodiment, a K-edge filter 122 is arranged outside the X-ray transmission window 113 in the X-ray source 111 having the configuration of the third embodiment.

The K-edge filter 122 attenuates the short-wavelength Kβ ray to a larger degree than the Kα ray of the characteristic X-rays 121 of the secondary target 119, while transmitting the Kα ray longer in wavelength. As a result, the Kα ray longer in wavelength is conspicuously increased in ratio, and the characteristic X-rays 121 having a high monochromaticity can be emitted.

As described above, there is provided a compact X-ray source 111 in which the endurance of the targets 118, 119 can be secured even against a large current, and large-output characteristic X-rays 121 can be emitted with a still higher monochromaticity.

Figure 7:
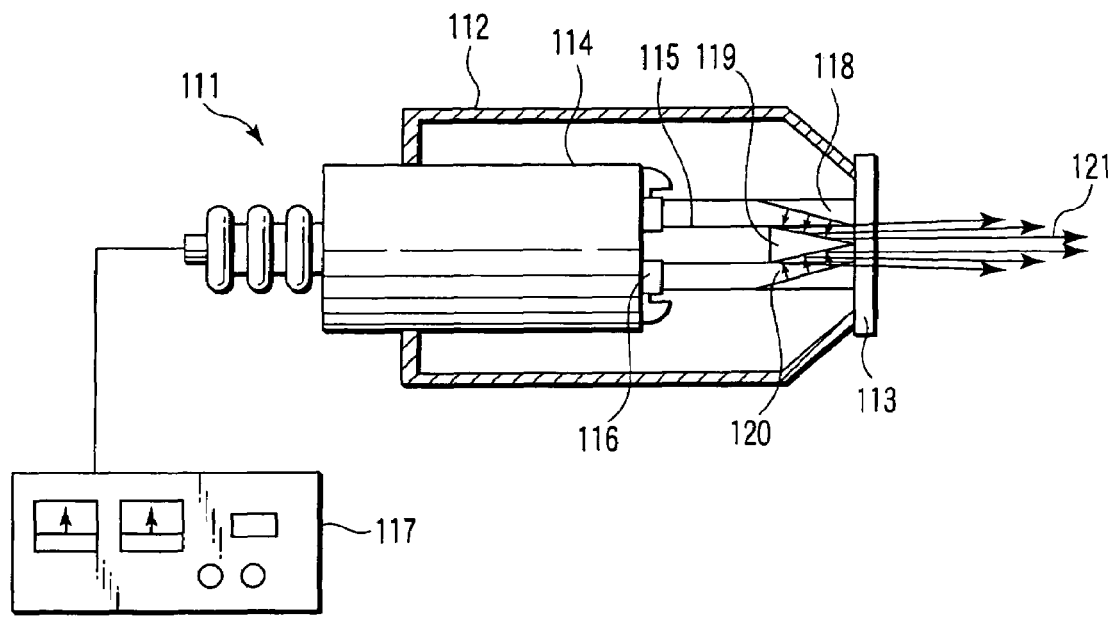
FIG. 7 is a diagram for explaining an X-ray source according to a fifth embodiment of the invention.

Next, a fifth embodiment is shown in FIG. 7.

According to this embodiment, the X-ray source 111 similar in configuration to the third embodiment includes an annular emitter 116 of the electron gun 114 for generating an annular electron beam 115. Also, the primary target 118 annular and coaxial with the annular electron beam 115 is entered by the annular electron beam 115 generated from the emitter 116 of the electron gun 114. Further, the secondary target 119 is arranged in opposed relation to the inner peripheral surface of the primary target 118 at the center thereof. The inner peripheral surface of the primary target 118 is tilted by being progressively expanded toward the electron gun to emit the continuous X-ray 120 in the direction of reflection toward the central secondary target 119. The secondary target 119 is in the shape of a cone and arranged with the top thereof facing the X-ray transmission window 113. For example, the surface of the secondary target 119, in parallel to the inner peripheral surface of the primary target 118, is configured in such a manner that the characteristic X-rays 121 excited by the continuous X-rays 120 incident from the primary target 118 are emitted in the direction of reflection toward the X-ray transmission window 113.

The annular electron beam 115 generated in the electron gun 114 passes around the primary target 118 and enters the inner peripheral surface of the primary target 118 thereby to emit the continuous X-ray 120 in the direction of reflection toward the surface of the secondary target 119 from the surface of the primary target 118. The continuous X-ray 120 emitted from the primary target 118 enters the surface of the secondary target 119, from which the characteristic X-rays 121 are emitted in the direction of reflection toward the X-ray transmission window 113. The characteristic X-rays 121 are emitted outside from the secondary target 119 through the X-ray transmission window 113.

Also in this case, the distance between the primary target 118 and the secondary target 119 is longer than in the first embodiment, and the efficiency of radiation and excitation of the secondary target 119 is reduced. By arranging the primary target 118 and the secondary target 119 in the vacuum container 112, however, the distance between the primary target 118 and the secondary target 119 can be shortened. Thus, the continuous X-ray 120 emitted from the primary target 118 can be efficiently used for excitation of the secondary target 119 and the characteristic X-rays 121 can be efficiently generated.

Also, as in the third embodiment, the primary target 118 can have a structure permitting a large heat capacity, in which the primary target 118 can be easily cooled through the vacuum container 112 and the X-ray transmission window 113. As a result, the current and energy of the incident electrons can be increased, thereby leading to the advantage of an increased continuous X-ray 120 generated and the resulting increase in the characteristic X-rays 121. Also, the characteristic X-rays 121 can be generated in spots. Further, the primary target 118 exhibits the function of a collimator for suppressing the spread of the characteristic X-rays 121. Advantageously, therefore, the characteristic X-rays 121 can be retrieved in the form of a beam small in dispersion angle and the background radiation of X-rays on other than the inspection points can be reduced.

As described above, there is provided a compact X-ray source 111 in which the large-dosage characteristic X-rays 121 can be retrieved as a beam.

Figure 8:
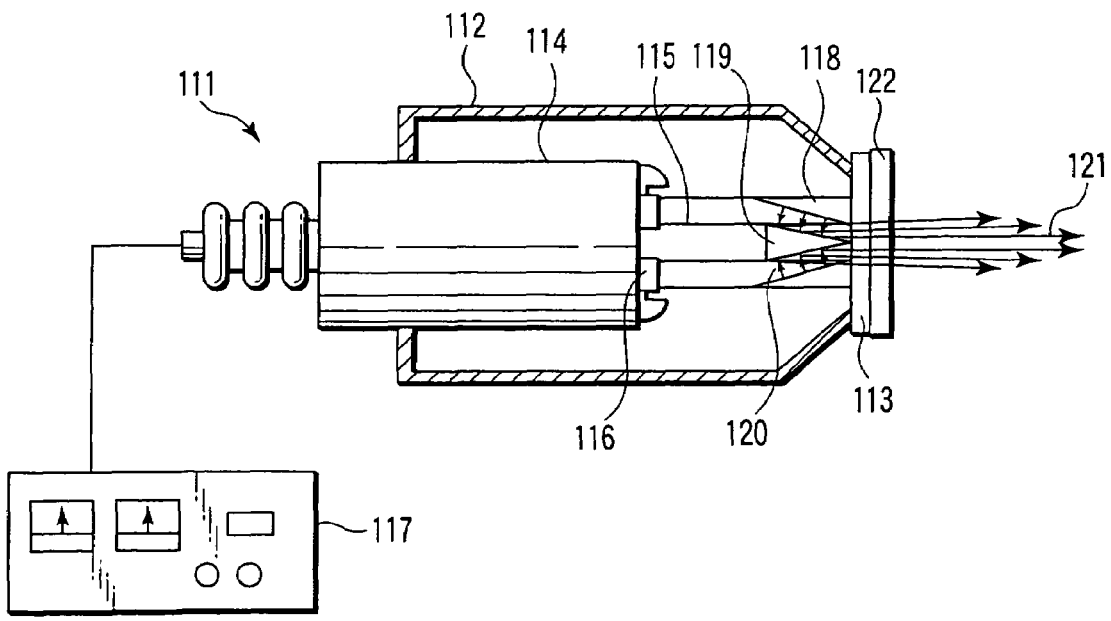
FIG. 8 is a diagram for explaining an X-ray source according to a sixth embodiment of the invention.

Next, a sixth embodiment is shown in FIG. 8.

According to this embodiment, the X-ray source 111 of the fifth embodiment is so configured that the K-edge filter 122 is arranged outside the X-ray transmission window 113.

The K-edge filter 122 has the effect of attenuating the short-wavelength Kβ ray to a larger degree than the Kα ray of the characteristic X-rays 121 of the secondary target 119, and transmits the long-wavelength Kα ray. Thus, the long-wavelength Kα ray conspicuously increases in ratio, thereby making it possible to emit the characteristic X-rays 121 high in monochromaticity.

In this way, there is provided a compact X-ray source 111 with an improved monochromaticity in which the characteristic X-rays 121 in large dosage can be retrieved as a beam.

Figure 9:
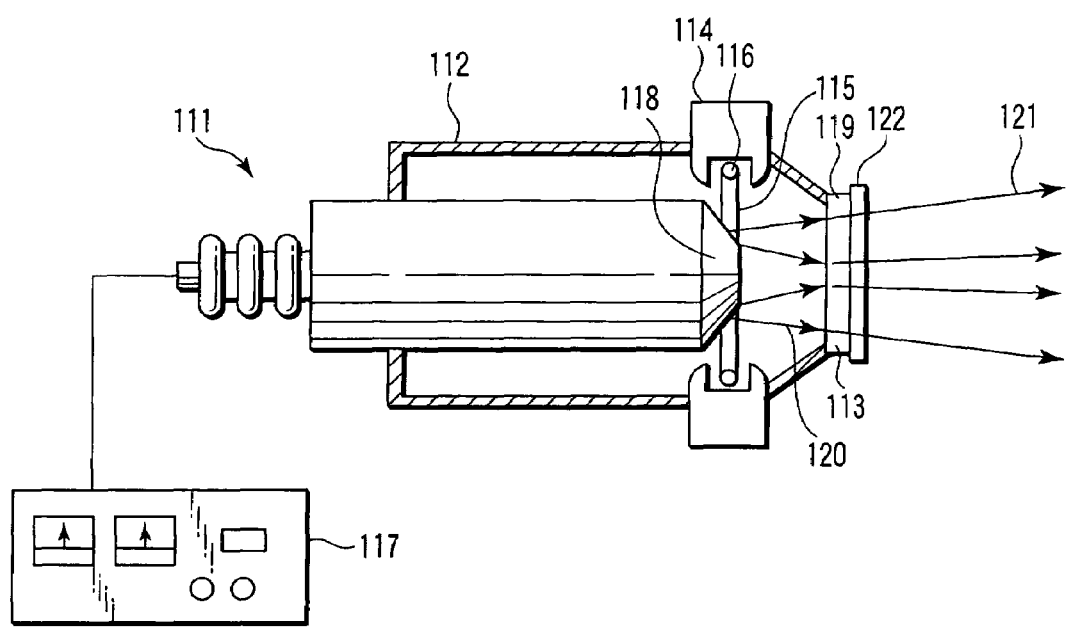
FIG. 9 is a diagram for explaining an X-ray source according to a seventh embodiment of the invention.

Next, a seventh embodiment is shown in FIG. 9.

According to this embodiment, unlike in the embodiments described above, the electron gun 114 is set at the earth potential and the primary target 118 at a high voltage.

The electron gun 114 suitably has an annular structure, and the primary target 118, being in the shape of a truncated cone, has the top thereof arranged in the direction toward the X-ray transmission window 113 at the center of the annular electron gun 114. The surface of the primary target 118 in the shape of a truncated cone is entered by the electron beam 115 from the electron gun 114 and the continuous X-ray 120 is emitted in the direction of reflection toward the X-ray transmission window 113.

The secondary target 119 is arranged in the X-ray transmission window 113, and the K-edge filter 122 outside the secondary target 119.

The electron beam 115 generated by the annular electron gun 114 enters the surface of the truncated-cone primary target 118, from which the continuous X-ray 120 is emitted in the direction of reflection toward the secondary target 119 of the X-ray transmission window 113. The continuous X-ray 120 emitted from the primary target 118 enters the secondary target 119, from which the characteristic X-rays 121 are transmitted and emitted.

The characteristic X-rays 121 emitted from the secondary target 119 are transmitted through the K-edge filter 122 of the X-ray transmission window 113 and emitted outside.

Also in this case, the distance between the primary target 118 and the secondary target 119 is longer than in the configuration of the first embodiment, and the efficiency of radiation and excitation of the secondary target 119 is reduced. Nevertheless, the distance between the primary target 118 and the secondary target 119, being arranged in the vacuum container 112, can be shortened. Thus, the continuous X-ray 120 emitted from the primary target 118 can be efficiently utilized for excitation of the secondary target 119 and the characteristic X-rays 121 can be generated efficiently.

Also, as in the third embodiment, the primary target 118 can have a structure permitting a large heat capacity. As a result, the current and energy of the incident electrons can be increased, thereby leading to the advantage of an increased continuous X-ray 120 generated and the resulting increase in the characteristic X-rays 121.

As described above, there is provided a compact X-ray source 111 with the negative electrode grounded in which the characteristic X-rays 121 having an intended energy can be efficiently emitted.

Incidentally, a material superior in X-ray transmission characteristic such as Be (beryllium) can be used for the X-ray transmission window 113, and the K-edge filter 122 can be attached to the exterior of the particular X-ray transmission window 113.

Next, an eighth embodiment is shown in FIGS. 10A and 10B.

According to this embodiment, the configuration of the X-ray source 111, though similar to that of the first embodiment, includes a secondary target unit 131 arranged in superposition on the outside of the primary target 118. This secondary target unit 131 has a plurality of secondary targets 119a, 119b, 119c and 119d capable of generating, for example, the characteristic X-rays 121 of different energy. The plurality of these secondary targets 119a to 119d are arranged equidistantly along the circumference of a rotary unit 133 rotatable around a rotary shaft 132.

The rotary shaft 132 of the rotary unit 133 is rotatable through a rotary mechanism making up a moving mechanism not shown, and one of the secondary targets 119a to 119d is selectively arranged at the position of X-ray generation of the primary target 118 in superposition on the primary target 118.

The provision of the plurality of the secondary targets 119a to 119d and the arrangement of an arbitrary one of the plurality of the secondary targets 119a to 119d at the position of X-ray generation of the primary target 118 eliminate the need of moving the X-ray source 111 to replace the secondary target. Therefore, the characteristic X-rays 121 of different energy can be readily retrieved advantageously without changing the position of X-ray generation. In the case where the X-ray source 111 is used for the fluorescent X-ray analyzing apparatus, therefore, analysis can be carried out without disturbing the measurement system including the position of X-ray generation and the specimen position.

As described above, there is provided a compact X-ray source 111 capable of selectively emitting the characteristic X-rays 12 of different energy without changing the position of X-ray generation.

Next, a ninth embodiment is shown in FIGS. 11A and 11B.

According to this ninth embodiment, the X-ray source 111 of the eighth embodiment includes a filter unit 135 arranged outside the secondary target unit 131. This filter unit 135 has K-edge filters 122a, 122b, 122c and 122d as filters corresponding to the secondary targets 119a to 119d, respectively, for generating, for example, the characteristic X-rays 121 of different energy. These K-edge filters 122a to 122d are arranged at positions corresponding to the secondary targets 119a to 119d along the same circumference of the rotary unit 136 rotatable around the rotary shaft 132. The rotary unit 133 of the secondary target unit 131 and the rotary unit 136 of the filter unit 135 may be integrated as a single disk or may be separate disks.

By arranging an arbitrary one of the plurality of the secondary targets 119a to 119d at the position of X-ray generation of the primary target 118, an arbitrary one of the corresponding K-edge filters 122a to 122d is also arranged. As a result, the X-ray source 111 is not required to be moved to replace the secondary target or the K-edge filter. As in the eighth embodiment, therefore, the characteristic X-rays 121 of different energy can be readily retrieved advantageously without changing the position of X-ray generation.

Also, the K-edge filters 122a to 122d have the effect of attenuating the short-wavelength Kβ ray to a larger degree than the Kα ray of the characteristic X-rays 121 of the secondary targets 119a to 119d, and act to transmit the long-wavelength Kα ray. Thus, the long-wavelength Kα ray is conspicuously increased in ratio and the characteristic X-rays 121 high in monochromaticity can be emitted.

As described above, there is provided a compact X-ray source 111 capable of producing the characteristic X-rays 121 high in monochromaticity by selectively emitting the characteristic X-rays 121 of different energy without changing the position of X-ray generation.

Next, a tenth embodiment is shown in FIGS. 12A and 12B.

According to this embodiment, like in the first embodiment, the configuration of the X-ray source 111 includes a target unit 141 arranged rotatably in the vacuum container 112. This target unit 141 has a plurality of sets of target portions 142a, 142b, 142c and 142d having different primary targets 118a, 118b, 118c and 118d and appropriate secondary targets 119a, 119b, 119c and 119d superposed and combined with each other, respectively. These primary targets 118a to 118d and secondary targets 119a to 119d are arranged equidistantly at the same positions on the same circumference of rotary units 144, 145 rotated around a rotary shaft 143. The rotary units 144, 145 may be integrated as a disk or may be separate disks.

A rotary mechanism 146 serving as a moving mechanism rotates the target unit 141 in the vacuum container 112 from outside the vacuum chamber 112.

The target unit 141 is arranged in such a manner as to rotate one of a plurality of sets of the target portions 142*a* to 142*d* around the rotary shaft 143 with respect to the position of the electron beam 115 incident from the electron gun 114. Thus, the primary targets 118*a* to 118*d* of the target portions 142*a* to 142*d* arranged at the position of electron beam incidence transmit and emit the continuous X-ray 120 in response to the incidence of the electron beam 115. At the same time, the secondary targets 119*a* to 119*d* transmit and emit from the X-ray transmission window 113 the characteristic X-rays 121 excited by the continuous X-ray 120 emitted from the primary targets 118*a* to 118*d*.

By selecting the target portions 142*a* to 142*d*, the characteristic X-rays 121 of selected energy can be readily retrieved, and at the time of this selection, the replacement of the X-ray source 111 is not required, thereby advantageously keeping the X-ray generation at a constant position.

Also, the function of the vacuum partition wall is provided by an independent X-ray transmission window 113, so that the thickness of the primary targets 118*a* to 118*d* and the secondary targets 119*a* to 119*d* can be arbitrarily selected.

As described above, there is provided a compact X-ray source 111 which can selectively emit several characteristic X-rays 121 without changing the position of X-ray generation.

Next, an eleventh embodiment is shown in FIG. 13.

According to this embodiment, the X-ray source 111 of the tenth embodiment includes a filter unit 148 arranged outside the secondary target unit 131. This filter unit 148 has K-edge filters 122*a*, 122*b*, 122*c* and 122*d* corresponding to the target portions 142*a* to 142*d*, respectively. These K-edge filters 122*a* to 122*d* are arranged at positions corresponding to the secondary targets 119*a* to 119*d* on the same circumference of a rotary unit 149 rotatable around the rotary shaft 143. The rotary shaft 143 is arranged through the X-ray transmission window 113.

With the provision of the K-edge filters 122*a* to 122*d*, the secondary targets 119*a* to 119*d* superposed with the primary targets 118*a* to 118*d* rotate integrally with the K-edge filters 122*a* to 122*d*, resulting in the advantage that several characteristic X-rays 121 improved in monochromaticity can be selectively emitted.

In this way, a compact X-ray source 111 is provided which can selectively emit several characteristic X-rays 121 high in monochromaticity without changing the position of X-ray generation.

Next, a twelfth embodiment is shown in FIG. 14.

According to this embodiment, the X-ray source 111 of the tenth embodiment is so configured that the target unit 141 has a plurality of sets of target portions 142*a*, 142*b*, 142*c* and 142*d* having different primary targets 118*a*, 118*b*, 118*c* and 118*d*, appropriate secondary targets 119*a*, 119*b*, 119*c* and 119*d* and appropriate K-edge filters 122*a*, 122*b*, 122*c* and 122*d* superposed and combined with each other.

The secondary targets 119*a* to 119*d* superposed on the primary targets 118*a* to 118*d* are rotated integrally with the K-edge filters 122*a* to 122*d*. Thus, characteristic X-rays 121 high in monochromaticity of different energy are obtained. At the same time, the integral rotation eliminates the drive unit outside the X-ray source 111, resulting in the advantage that the X-ray source 111 can be arranged more reliably in proximity to the specimen.

As described above, there is provided a highly reliable compact X-ray source 111 in which several characteristic X-rays 121 high in monochromaticity can be emitted selectively without changing the position of X-ray generation.

Incidentally, according to this embodiment, the target portions 142*a* to 142*d* may be moved with respect to the position of electron beam incidence not necessarily by rotation but by sliding.

Next, a thirteenth embodiment is shown in FIG. 15.

According to this embodiment, like in the eighth embodiment, the X-ray source 111 is so configured that the X-ray transmission window 113 is rotatable with respect to the vacuum container 112. The inner surface of the X-ray transmission window 113 is formed with the target unit 141 having a plurality of sets of the target portions 142*a*, 142*b*, 142*c* and 142*d* having the different primary targets 118*a*, 118*b*, 118*c* and 118*d* and appropriate secondary targets 119*a*, 119*b*, 119*c* and 119*d* superposed and combined with each other.

With the rotation of the X-ray transmission window 113, an arbitrary one of the plurality of sets of the target portions 142*a* to 142*d* of the target unit 141 can be arranged with respect to the position of the electron beam 115 incident from the electron gun 114. Thus, the primary targets 118*a* to 118*d* of the target portions 142*a* to 142*d* arranged at the position of the electron beam incidence transmit and emit the continuous X-ray 120 in response to the incidence of the electron beam 115. At the same time, the secondary targets 119*a* to 119*d* transmit and emit from the X-ray transmission window 113 the characteristic X-rays 121 excited by the continuous X-ray 120 emitted from the primary targets 118*a* to 118*d*.

By selecting the target portions 142*a* to 142*d*, the characteristic X-rays 121 of selected energy can be readily retrieved. At the same time, by rotating the target unit 141 integrally, the primary targets 118*a* to 118*d* heated by the electron beam 115 are cooled by heat conduction to the X-ray transmission window 113, thereby advantageously leading to a long service life.

As described above, a compact X-ray source 111 long in service life is provided in which several characteristic X-rays 121 high in monochromaticity can be selectively emitted without changing the position of X-ray generation.

Next, a fourteenth embodiment is shown in FIG. 16.

According to this embodiment, the X-ray source 111 of the thirteenth embodiment has a plurality of sets of target portions 142*a*, 142*b*, 142*c* and 142*d* having different primary targets 118*a*, 118*b*, 118*c* and 118*d*, appropriate secondary targets 119*a*, 119*b*, 119*c* and 119*d* and appropriate K-edge filters 122*a*, 122*b*, 122*c* and 122*d* superposed and combined with each other.

The secondary targets 119*a* to 119*d* superposed with the primary targets 118*a* to 118*d* are rotated integrally with the K-edge filters 122*a* to 122*d*. Thus, the characteristic X-rays 121 high in monochromaticity of different energy can be obtained, and at the same time, by the integral rotation, the primary targets 118*a* to 118*d* heated by the electron beam 115 are cooled by the heat conduction to the X-ray transmission window 113 thereby to advantageously lengthen the service life.

As described above, there is provided a compact X-ray source 111 having a long service life which can emit several characteristic X-rays 121 high in monochromaticity without changing the position of X-ray generation.

Next, FIG. 17 shows a fluorescent X-ray analyzing apparatus 161 using the X-ray source 111 according to each embodiment described above.

The fluorescent X-ray analyzing apparatus 161 is so configured that the characteristic X-rays 121 emitted from the X-ray source 111 are irradiated on a specimen 162 and a fluorescent X-ray 163 generated by excitation of the elements on the surface of the specimen 162 is captured by an energy discrimination type X-ray detector 165 through a collimator 164 thereby to analyze the elements.

The X-ray source 111 used for the fluorescent X-ray analyzing apparatus 161 has an energy spectrum mainly composed of the characteristic X-rays (Kα and Kβ rays) 121 of the secondary targets 119a to 119d, whereby the fluorescent X-ray 163 generated by excitation of the elements on the surface of the specimen 162 is captured, thereby making it possible to analyze the element composition.

In the process, the spectrum of the characteristic X-rays 121 excited is stored in an analysis device in advance, and the resulting relation between the fluorescent signal and the excitation strength is determined. In this way, the quantitative analysis of the elements on the surface of the specimen 162 can be carried out accurately based on the strength of the fluorescent signal.

Also, the use of the X-ray source 111 having the primary targets 118a to 118d, the secondary targets 119a to 119d and the K-edge filters 122a to 122d in rotation makes it possible to select the energy of the characteristic X-rays 121 used for excitation according to the atomic number of the elements contained in the intended specimen 162 without replacing the X-ray source 111.

As described above, a high-resolution fluorescent X-ray analyzing apparatus 161 is provided by the X-ray source 111 capable of efficiently emitting the characteristic X-rays 121.

Next, another example of the fluorescent X-ray analyzing apparatus 161 is shown in FIG. 18.

This fluorescent X-ray analyzing apparatus 161, including a plurality of X-ray sources 111, is so configured that the characteristic X-rays 121 emitted from one of the X-ray sources 111 are irradiated on the specimen 162 and the fluorescent X-ray 163 is captured by the X-ray detector 165 of energy discrimination type through the collimator 164 thereby to analyze the elements.

Like the fluorescent X-ray analyzing apparatus 161 described above, the fluorescent X-ray 163 generated by excitation of the elements on the surface of the specimen 162 by the characteristic X-rays (Kα and Kβ rays) 121 of one of the X-ray sources 111 in use is captured, and thus the element composition can be analyzed. Further, by switching to the characteristic X-rays 121 from another X-ray source 111, the composition of the elements in a wide range of atomic numbers can be analyzed within a short time.

In this way, a fluorescent X-ray analyzing apparatus 161 which can analyze the elements with high resolution within a short time is provided by the X-ray source 111 capable of efficiently emitting the characteristic X-rays 121.

Figure 19:
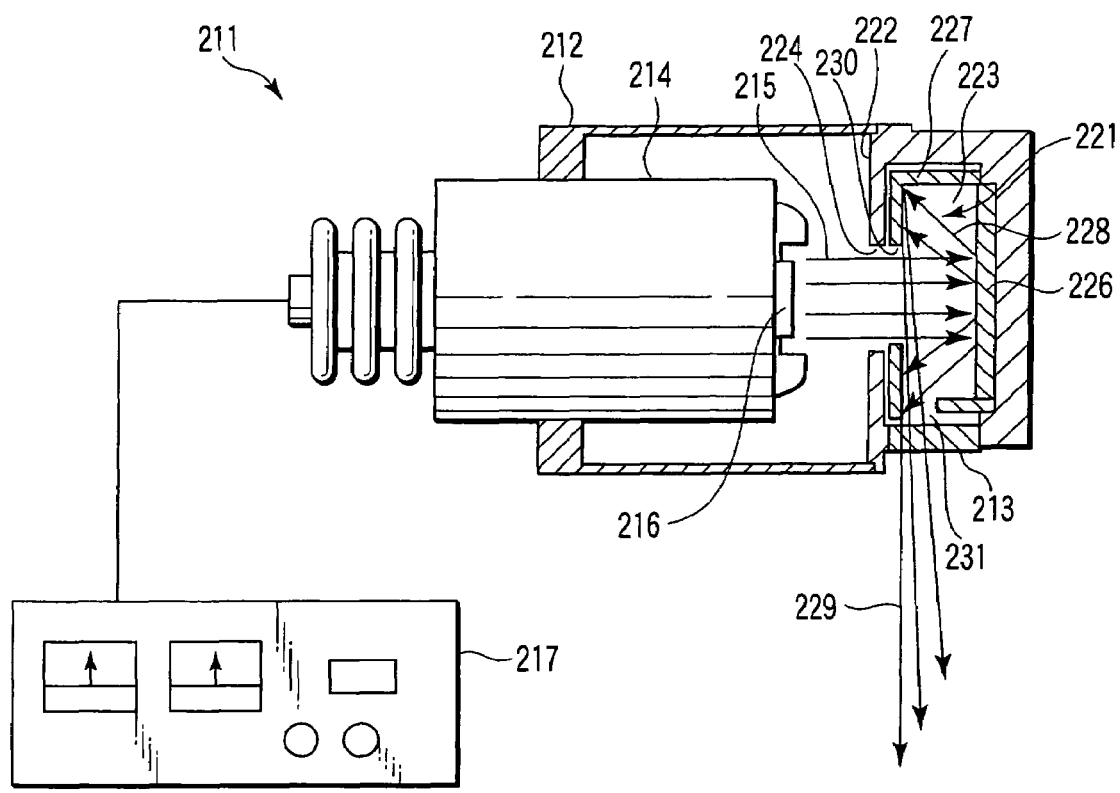
FIG. 19 is a diagram for explaining an X-ray source according to a fifteenth embodiment of the invention.
Figure 20:
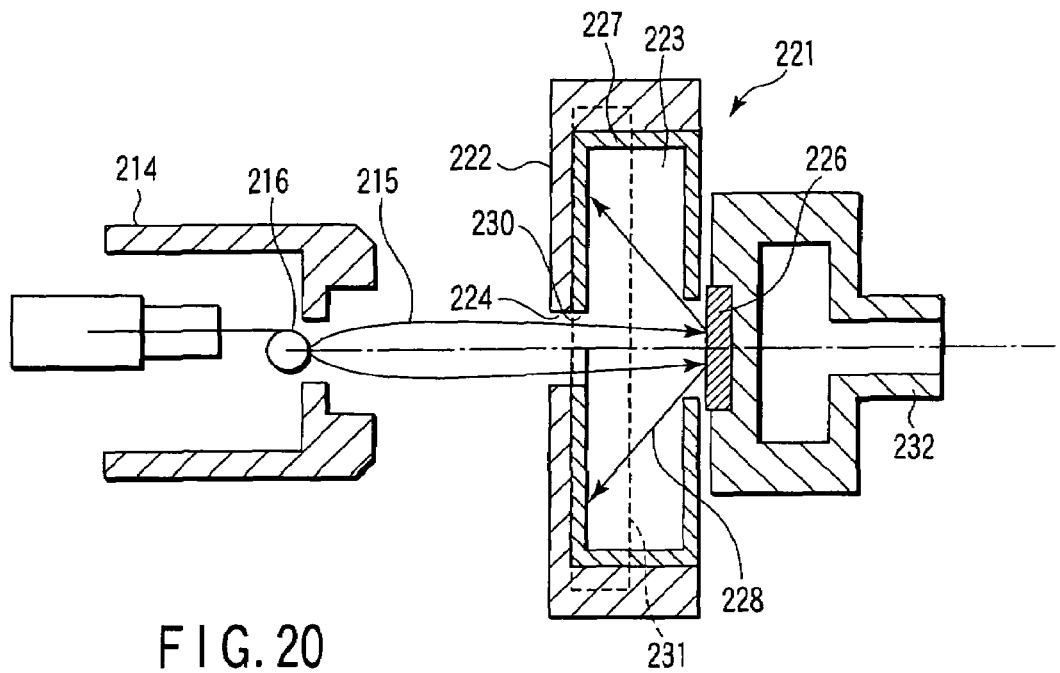
FIG. 20 is a diagram for explaining the relation between an electron gun and an X-ray generating unit of the X-ray source.
Figure 21:
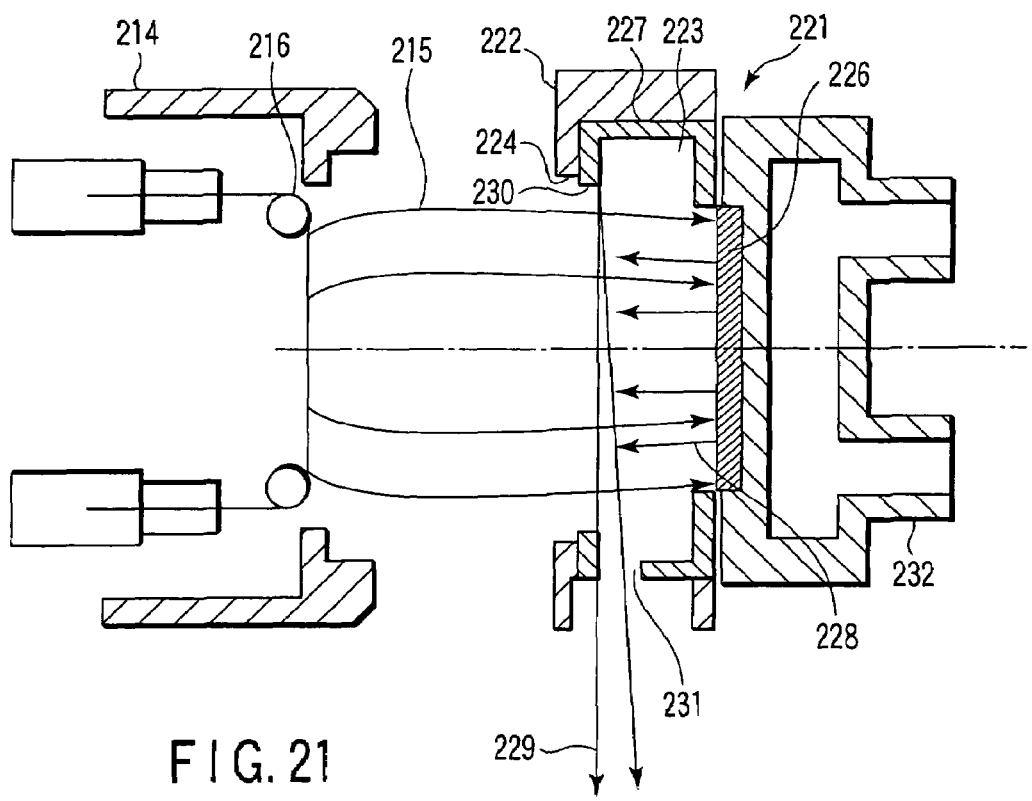
FIG. 21 is a diagram for explaining the relation between the electron gun and the X-ray generating unit of the X-ray source as viewed from a direction differing by 90° from that in FIG. 20.

A fifteenth embodiment is shown in FIGS. 19 to 21.

An X-ray source 211 includes a vacuum container 212 with the interior thereof held in a vacuum, and an X-ray transmission window 213 for emitting the X-rays outside is arranged on the side surface at one end of the vacuum container 212.

An electron gun 214 is arranged at the other end of the vacuum container 212, and a filament 216 constituting an emitter for emitting an electron beam 215 toward one end in the vacuum container 212 is arranged at the end of the electron gun 214 located in the vacuum container 212. The filament 216 is formed in a line and capable of emitting a thin linear electron beam 215. The electron gun 214 generates and accelerates the electron beam 215 through a drive power supply 217.

A box-type X-ray generating unit 221 is defined and formed at an internal end of the vacuum container 212.

A defined portion 223 is formed in the X-ray generating unit 221 by a wall portion 222 defining the interior of the vacuum container 212. The surface of the wall portion 222 in opposed relation to the electron gun 214 is formed with a slit-like electron beam passage hole 224 in a shape corresponding to the linear electron beam 215 generated by the electron gun 214, through which hole 224 the electron beam 215 can easily pass. The X-ray transmission window 213 is arranged on the surface crossing the surface of the defined portion 223 formed with the electron beam passage hole 224.

The inner surface of the defined portion 223 in opposed relation to the electron beam passage hole 224 is formed with a primary target 226, and the greater part of the inner surface of the defined portion 223 other than the primary target 226 is formed with a box-type secondary target 227.

The primary target 226 is entered by the electron beam 215 passed through the electron beam passage hole 224 and emits a continuous X-ray 228 as a primary X-ray toward the secondary target 227.

The secondary target 227, entered by the continuous X-ray 228 emitted from the primary target 226, emits characteristic X-rays 229 as K rays constituting the secondary X-rays. The secondary target 227 is formed with a slit-like electron beam passage hole 230 in the shape corresponding to the linear electron beam 215 generated by the electron gun 214, through which hole 230 the electron beam 215 can easily pass. That surface crossing the surface formed with the electron beam passage hole 230 which is in opposed relation to the X-ray transmission hole 213 is formed with an X-ray passage hole 231 for emitting the characteristic X-rays 229. The X-ray passage hole 231 is formed as an elongate slit permitting the retrieval of the characteristic X-ray 229 in the form of a sheet beam not mixed with the continuous X-ray 228.

The secondary target 227 is in such a shape that the primary target 226 and the secondary target 227 are arranged in narrowly opposed relation in the direction in which the electron beam 215 passes in a short distance from the electron beam passage hole 230 to the primary target 226. With this configuration, the continuous X-ray 228 emitted from the primary target 226 can be rendered to enter the secondary target 227 at a wide angle for an improved excitation efficiency of the secondary target 227.

The primary target 226 is also formed as a thin line conforming with the shape of the electron beam 215 passing through the electron beam passage hole 230 of the secondary target 227, and in the case where an electron beam high in strength is applied, the primary target 226 is mounted on a cathode structure having a water-cooled jacket 232 to remove heat.

The electron beam 215 emitted by application of a voltage from the drive power supply 217 to the electron gun 214 is passed through the electron beam passage hole 230 of the box-like secondary target 227 and enters the primary target 226 arranged in opposed relation to the electron beam passage hole 230. In the process, the secondary target 227 is irradiated and excited by the continuous X-ray 228 emitted from the primary target 226 in opposed relation to the secondary target 227 thereby to emit the characteristic X-rays 229. Only the components of the characteristic X-rays 229 emitted at a small angle from the surface of the secondary target 227 are passed through the X-ray passage hole 231 while at the same time being emitted outside through the X-ray transmission window 213.

In this way, there is provided an X-ray source 211 for producing the characteristic X-rays 229 in the form of a sheet beam while suppressing the intrusion of the noise components other than the characteristic X-rays 229 to be used.

Incidentally, all the component members of the box-like secondary target 227 are not necessarily formed of the materials of the secondary target. For example, an ordinary material such as stainless steel may be used as a main component material, and foils of the materials of the secondary target may be attached or coated only on the inner surface portion entered by the continuous X-ray 228.

Figure 22:
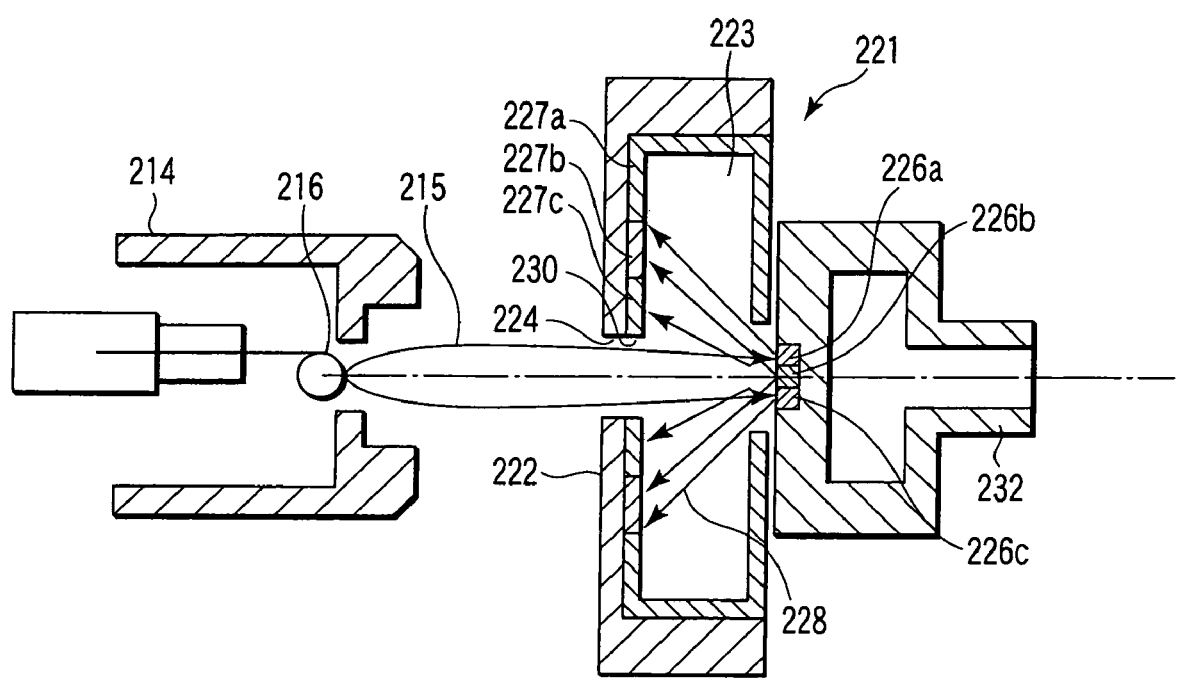
FIG. 22 is a diagram for explaining an X-ray source according to a sixteenth embodiment of the invention.

Next, a sixteenth embodiment is shown in FIG. 22.

According to this embodiment, primary targets 226a, 226b and 226c of the X-ray source 211 of the first embodiment are configured of a plurality of materials (elements), while at the same time using a plurality of materials (atoms) for opposed secondary targets 227a, 227b and 227c irradiated with the continuous X-ray 228.

For excitation using the X-rays, the primary targets 226a to 226c for emitting the continuous X-ray 228 to excite the secondary target 227 can be formed of an element larger in atomic number by about 2 than the secondary targets 227a to 227c, and the characteristic X-rays 229 emitted thereby may be used to excite the secondary target 227 most efficiently.

In order to obtain the intended characteristic X-ray 229 for this purpose, assume that a plurality of secondary targets 227a to 227c are used. It is necessary to select the primary targets 226a to 226c of the optimum element to excite each element.

For example, as a combination that can be employed, chromium (Cr: Kα energy of characteristic X-ray is 5.4 keV) may be used as the primary targets 226a to 226c for titanium (Ti: Kα energy of characteristic X-ray is 4.5 keV) of the secondary targets 227a to 227c, rhodium (Rh: Kα energy of characteristic X-ray is 20.2 keV) as the primary targets 226a to 226c for molybdenum (Mo: Kα energy of characteristic X-ray is 17.5 keV) of the secondary targets 227a to 227c, or tantalum (Ta: Kα energy of characteristic X-ray is 57.5 keV) as the primary targets 226a to 226c for gadolinium (Gd: Kα energy of characteristic X-ray is 43 keV) of the secondary targets 227a to 227c. As a result, an X-ray beam containing the three characteristic X-rays of Cr, Mo and Gd (4.5 keV, 17.5 keV, 43 keV) 29 at the same time can be emitted.

In the case where the X-ray of single energy is used for excitation in the fluorescent X-ray analysis, therefore, the types of elements that can be excited thereby are limited. Nevertheless, the X-ray including a plurality of monochromatic energy components covering low to high energy areas can be used, and a wide area of element analysis can be employed.

As described above, there is provided an X-ray source 211 capable of emitting the characteristic X-rays 229 containing the characteristic X-ray spectra of a plurality of energy with few noise components.

Next, a seventeenth embodiment is shown in FIGS. 23A, 23B, 23C and 23D.

This embodiment concerns a method of operation of the X-ray source 211 of the sixteenth embodiment so configured to contain a combination of a plurality of primary targets 226a to 226c and a plurality of secondary targets 227a to 227c.

In order to most efficiently excite the secondary targets 227a to 227c selected as a combination by the continuous X-ray 228 emitted from the primary targets 226a to 226c, it is important that the electron beam 215 irradiated on the primary targets 226a to 226c has sufficient energy to emit the continuous X-ray 228 sufficiently from the primary targets 226a to 226c.

Generally, the continuous X-ray 228 of the primary targets 226a to 226c can be emitted most efficiently by excitation using the electron beam 215 of an energy double or triple that of the K-ray energy of the primary targets 226a to 226c, so that the characteristic X-rays 229 of the secondary targets 227a to 227c can be most efficiently emitted.

In the case where the continuous X-ray 228 from the primary targets 226a to 226c fails to reach the K-shell absorption end energy of the secondary targets 227a to 227c, on the other hand, the characteristic X-rays 229 cannot be emitted from the secondary targets 227a to 227c.

Taking advantage of this feature, the operation method becomes possible to adjust the acceleration voltage of the electron beam 215, i.e. the energy of the electron beam 215 in accordance with the energy of the characteristic X-rays 229 selected.

FIGS. 23A, 23B, 23C and 23D show the method of controlling the spectral distribution of the characteristic X-rays 229 emitted. In the case where the source voltage is increased and the high-energy electron beam 215 is used for excitation, as shown by the target D, etc., the primary targets 226a to 226c of high atomic numbers can be excited most efficiently, and the strength of the resulting characteristic X-rays 229 emitted from the secondary targets 227a to 227c can be increased. Conversely, as shown by the target A, etc., the strength of the continuous X-ray 228 emitted from the primary targets 226a to 226c low in atomic number is low, and therefore, the strength of the characteristic X-rays 229 from the secondary targets 227a to 227c in combination is reduced.

By progressively reducing the source voltage, as shown by the targets D and C, the spectral strength of the characteristic X-rays 229 on the high energy side is reduced, while as shown by the targets C and B, the spectral strength of the low-energy characteristic X-rays 229 increases. Further, as the source voltage continues to be decreased, as shown by the targets D and C, the high-energy spectrum soon disappears, and as shown by the targets B and A, only the X-ray spectrum on the low-energy side can be emitted.

In the fluorescent X-ray analysis, the distribution of this X-ray spectrum is controlled so that the signals of the fluorescent X-rays from the specimen containing the elements of low to high atomic numbers can be discriminated, which enables an accurate analysis result to be effectively obtained.

In this way, there is provided an X-ray source 211 in which the spectral distribution of the emitted characteristic X-rays 229 can be adjusted using the X-ray source 211 capable of emitting the characteristic X-rays 229 containing the characteristic X-ray spectra of a plurality of energy with few noise components.

Figure 24:
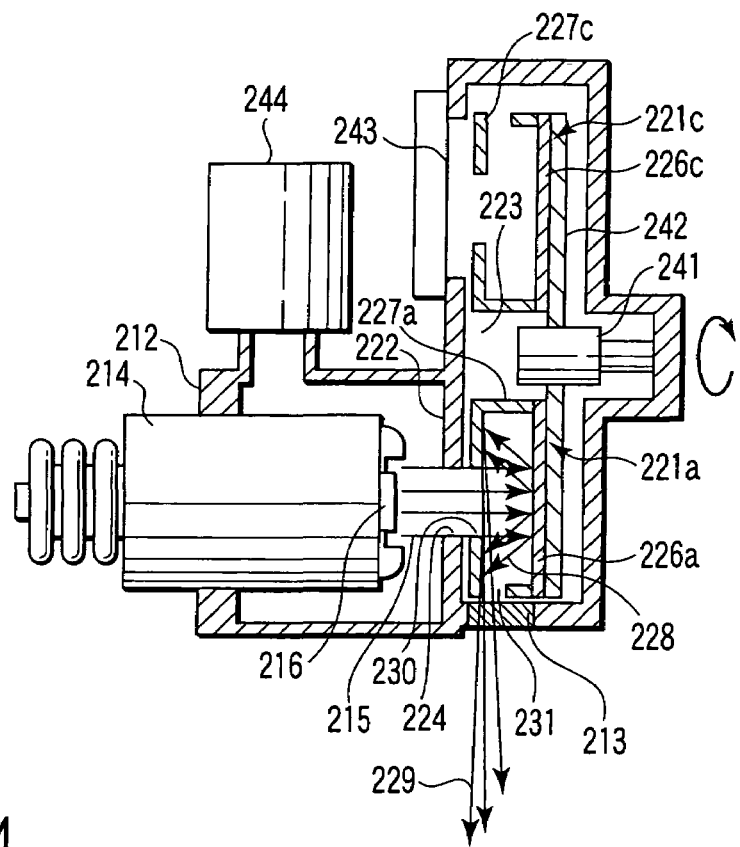
FIG. 24 is a diagram for explaining an X-ray source according to an eighteenth embodiment of the invention.
Figure 25:
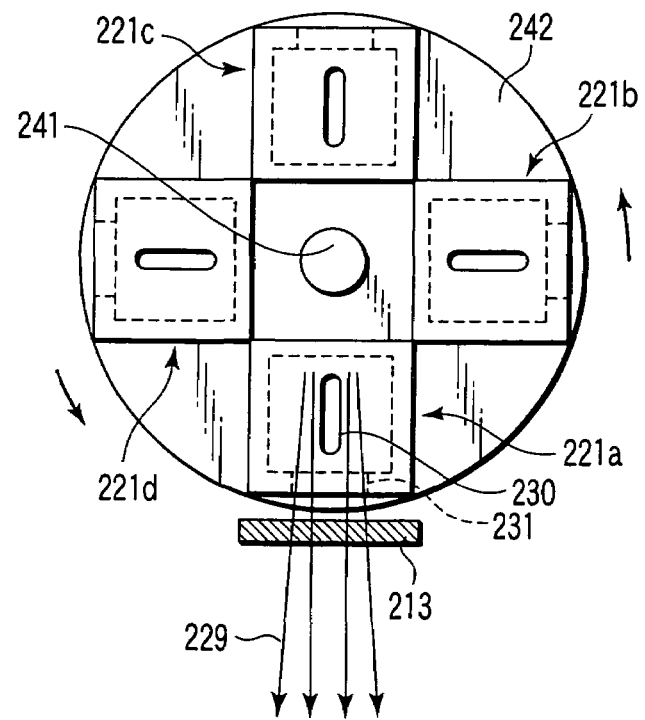
FIG. 25 is a diagram for explaining the target of the same X-ray source.

Next, an eighteenth embodiment is shown in FIGS. 24 and 25.

In the X-ray source 211 according to the sixteenth embodiment, the characteristic X-rays 229 can be emitted at the same time from the plurality of the primary targets 226a to 226c and the secondary targets 227a to 227c. Since the electron beam 215 is irradiated by dispersion on the number of the primary targets 226a to 226c installed, however, the strength of each characteristic X-ray 229 can be increased.

According to this eighteenth embodiment, on the other hand, a plurality of X-ray generating units 221a to 221d making up a plurality of sets of units including combinations of the primary targets 226a to 226d and the secondary targets 227a to 227d are used and arranged on the same circumference of a turntable 242 rotated by a rotary mechanism 241. An arbitrary one of the X-ray generating units 221a to 221d can be selected and moved by the rotary mechanism 241 with respect to the position of incidence of the electron beam 215. In this way, the characteristic X-rays 229 emitted can be changed.

Also, the vacuum container 212 includes a target change port 243 adapted to replace the X-ray generating units 221a to 221d and a vacuum pump 244 for exhausting the vacuum container 212. Even in the case where the required X-ray energy undergoes a change, therefore, the X-ray generating units 221a to 221d can be used by replacement.

By employing this configuration, the emitted characteristic X-rays 229 can be used selectively and sequentially. In the fluorescent X-ray analysis, the radiation and analysis of the characteristic X-rays 229 one by one effectively contributes to accurate identification of the elements in the specimen.

In this way, an X-ray source 211 is provided, in which a plurality of characteristic X-rays 29 few in noise components and high in strength can be arbitrarily selected and retrieved.

Figure 26:
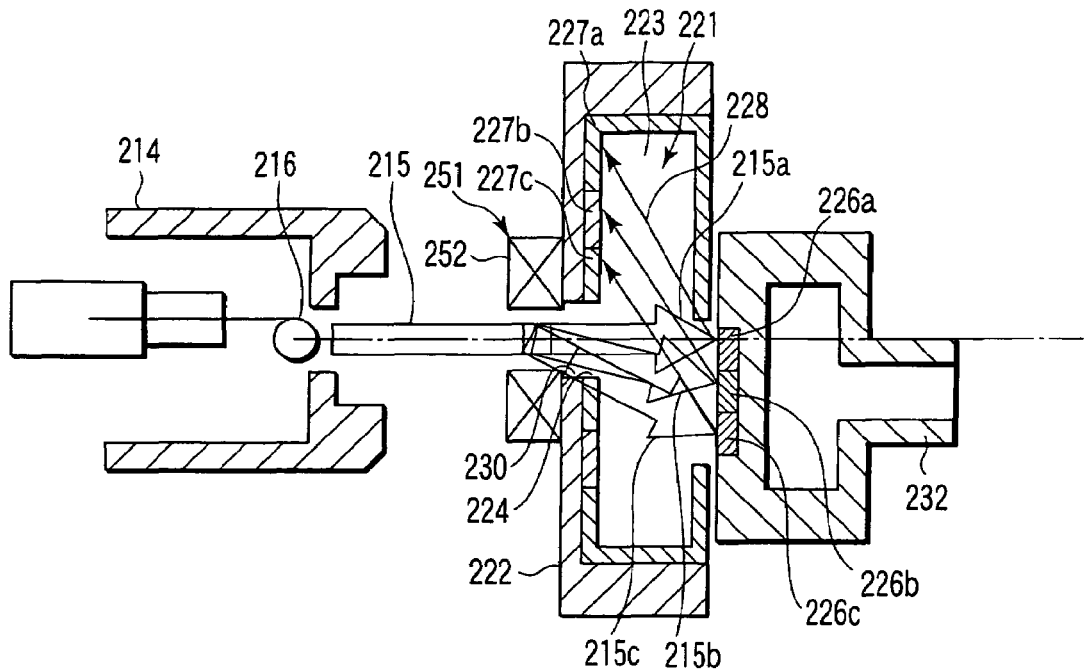
FIG. 26 is a diagram for explaining an X-ray source according to a nineteenth embodiment of the invention.

Next, a nineteenth embodiment is shown in FIG. 26.

According to this embodiment, the configuration of the X-ray source 211 of the sixteenth embodiment includes a deflection magnet 252 of electron beam deflection means 251 installed upstream, in the direction of passage of the electron beam, of the electron beam passage hole 224 of the wall portion 222 of the defined portion 223 making up the anode and the electron beam passage hole 230 of the secondary targets 227a to 227c.

In this configuration, the use of an electromagnet as the deflection magnet 252 can change the trajectory of the electron beam 215 such as shown by electron beams 215a, 215b, 215c by controlling the magnetic field strength, so that different primary targets 226a to 226c can be irradiated, respectively.

In the case where a permanent magnet is used as the deflection magnet 252, on the other hand, the trajectory can be changed similarly such as shown by the electron beams 215a to 215c by changing the energy of the passing electron beam 215.

In the case where the voltage of the drive power supply 217 is reduced and the low-energy electron beam 215 is used, the trajectory is greatly curved like the electron beam 215c with the same magnetic field strength, and an intended primary target 226c is arranged at the terminal end thereof. In a similar fashion, as far as the high-energy electron beam 215 is concerned, the trajectory is deflected to a lesser degree such as shown by the electron beams 215b, 215a, so that the primary targets 226b, 226a are arranged at the individual terminal ends. By employing this configuration, different primary targets can be irradiated by the electron beam in accordance with the voltage of the drive power supply 217, and therefore, it is possible to emit the continuous X-ray 228 higher in strength than in the configuration of the second embodiment in which the electron beam is irradiated on several types of primary targets at the same time. As a result, the X-ray spectrum obtained by voltage control as shown in the seventeenth embodiment can be distributed with more emphasis on strong and weak points.

As described above, there is provided an X-ray source 211 in which the spectral distribution including a plurality of the characteristic X-rays 229 can be retrieved with low noise while being controlled by voltage.

Figure 27:
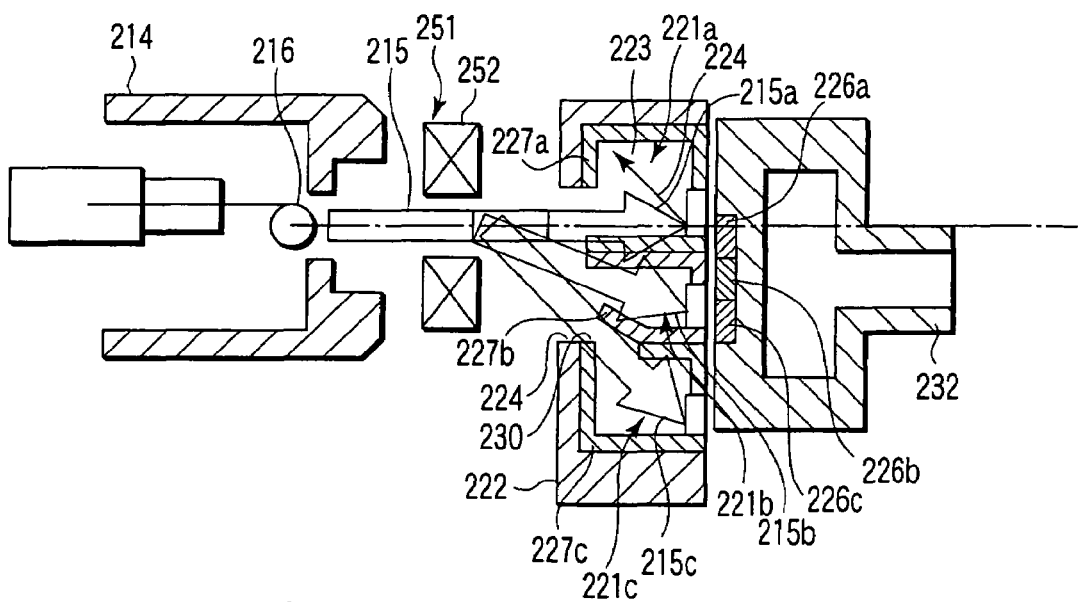
FIG. 27 is a diagram for explaining an X-ray source according to a twentieth embodiment of the invention.

Next, a twentieth embodiment is shown in FIG. 27.

According to this embodiment, the X-ray source 211 of the nineteenth embodiment is so configured that the primary targets 226a to 226c and the secondary targets 227a to 227c are divided into X-ray generating units 221a to 221c independent of each other. The electron beam 215, of which the trajectory is curved by the deflection magnet 252, enters the primary targets 226a to 226c of an arbitrary one of the X-ray generating units 221a to 221c.

Assume, for example, that the energy of the electron beam 215a and the magnetic field strength of the deflection magnet 252 are set in such a manner that the electron beam 215a enters the primary target 226a of the X-ray generating unit 221a. The continuous X-ray 228 that has entered the primary target 226a of the X-ray generating unit 221a excites an independent box-like secondary target 227a while the secondary targets 227b, 227c of the other X-ray generating units 221b, 221c are not entered or excited. As a result, as long as the characteristic X-ray 229 is emitted from any one of the X-ray generating units 221a to 221c, the other characteristic X-rays 229 are not emitted, and therefore, only a single characteristic X-ray 229 can be used.

In the fluorescent X-ray analysis, therefore, the characteristic X-rays 229 of low to high energy can be irradiated for excitation sequentially on the specimen, and therefore, the elements in the specimen can be easily identified.

As described above, there is provided an X-ray source 211 capable of retrieving a plurality of characteristic X-rays 229 one by one arbitrarily with low noise by controlling the voltage and the magnetic field strength.

Figure 28:
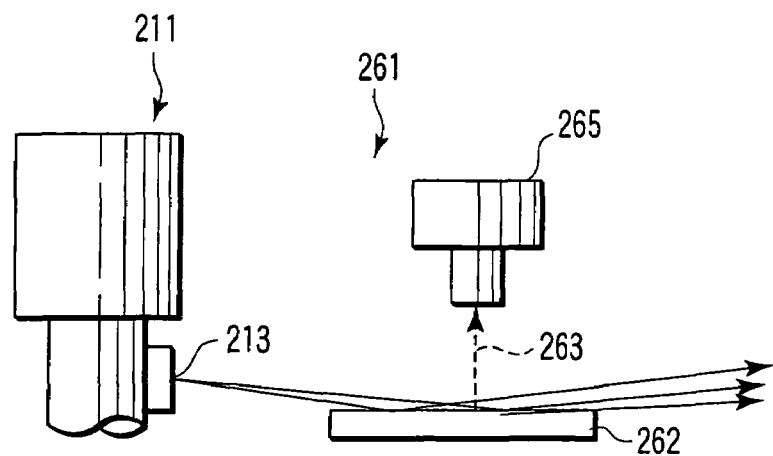
FIG. 28 is a diagram for explaining the fluorescent X-ray analyzing apparatus using the X-ray source according to the invention.
Figure 29:
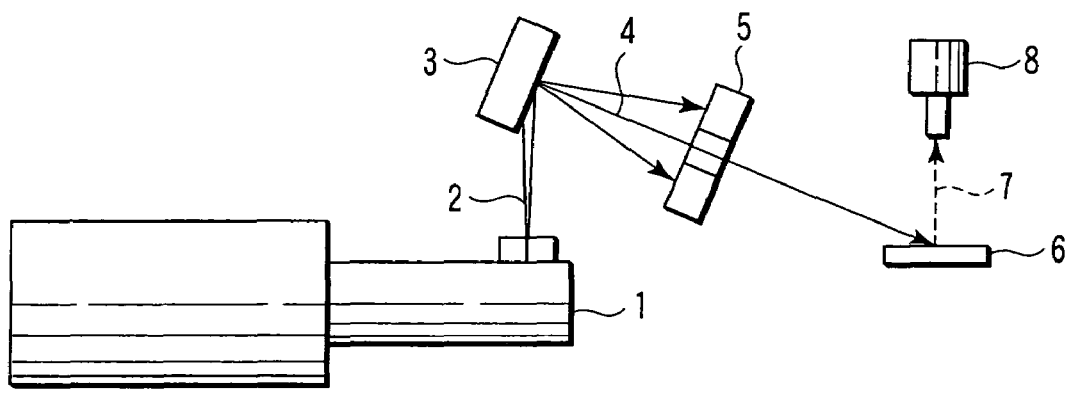
FIG. 29 is a diagram for explaining the conventional fluorescent X-ray analyzing apparatus.
Figure 30:
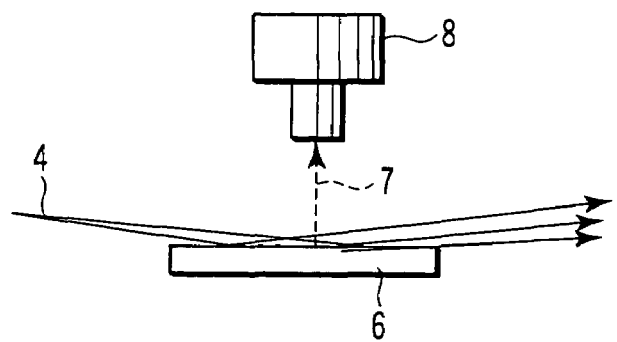
FIG. 30 is a diagram for explaining the conventional total reflection X-ray fluorescence analyzing method.

Next, a fluorescent X-ray analyzing apparatus 261 using the X-ray source 211 according to the aforementioned embodiments is shown in FIG. 28.

The fluorescent X-ray analyzing apparatus 261 is so configured that the characteristic X-rays 229 in the form of a sheet beam emitted from the X-ray source 211 are irradiated on the specimen 262, and a fluorescent X-ray 263 generated by excitation of the elements on the surface of the specimen 262 is captured by an X-ray detector 265 thereby to analyze the elements.

In the case where the inspection of the surface contamination of a semiconductor wafer as a specimen 262 is intended, the characteristic X-rays 229 are required to enter the surface of the semiconductor wafer at as constant an angle as possible as small as not more than 0.1° to the surface of the semiconductor wafer. The characteristic X-rays 229, therefore, assume a form of a sheet beam containing a sectorial fan beam or the like.

The X-ray source 211 used for the fluorescent X-ray analyzing apparatus 261 has an energy spectrum mainly composed of the characteristic X-rays 229 of the secondary targets 227, 227a to 227d, whereby the fluorescent X-ray 263 generated by excitation of the elements on the surface of the specimen 262 is captured thereby to analyze the element composition.

In the process, the spectrum of the characteristic X-ray 229 excited is stored beforehand in an analyzing device, and the relation between the fluorescent signal and the excitation strength is determined. In this way, from the fluorescent signal strength, the quantitative analysis of the elements on the surface of the specimen 262 can be carried out accurately.

As described above, there is provided a fluorescent X-ray analyzing apparatus 261 of high resolution by the X-ray source 211 capable of emitting the characteristic X-rays 229 in the form of a sheet beam efficiently.

According to this invention, there is provided an X-ray source and a fluorescent X-ray analyzing apparatus using the X-ray source in which the primary targets and the secondary targets are superposed on one another, so that the X-ray emitted from the primary targets can be efficiently used for excitation of the secondary targets, and the characteristic X-rays can be generated efficiently.

Also, according to this invention, there is provided an X-ray source and a fluorescent X-ray analyzing apparatus using the X-ray source, wherein the primary targets and the secondary targets are arranged in a vacuum container, and therefore, the distance between the primary and secondary targets can be shortened, so that the X-ray emitted from the primary targets can be efficiently used for excitation of the secondary targets, thereby making it possible to efficiently generate the characteristic X-ray, and wherein in view of the fact that the X-ray is emitted in the direction of reflection on the primary targets by the electron beam, the heat shock resistance is higher than in the X-ray transmission system, and therefore, the output can be increased due to a higher current being used to power the electron beam.

Also, according to this invention, there is provided an X-ray source and a fluorescent X-ray analyzing apparatus using the X-ray source, wherein the primary and secondary targets are built in a vacuum container, and therefore, the characteristic X-ray can be emitted at high efficiency, and wherein the intrusion of noise components into the emitted characteristic X-ray is suppressed while at the same time making it possible to easily produce the characteristic X-ray in the form of a sheet beam suited to, for example, total reflection fluorescent X-ray analysis.

What is claimed is:

1. An X-ray source comprising:
   a vacuum container having an X-ray transmission window;
   an electron gun which generates an electron beam in the vacuum container;
   an unshielded primary target having an angled outer surface and positioned within the vacuum container and entered by the electron beam from the electron gun to emit an X-ray; and
   a cylindrically shaped secondary target arranged in opposed relation to the primary target and surrounding the primary target within the vacuum container,
   wherein the secondary target is configured with an inner peripheral surface that is parallel to the angled outer surface of the primary target, so that a characteristic X-ray generated by the secondary target, due to the excitation of the X-ray emitted from the primary targets, is emitted toward the X-ray transmission window.

2. The X-ray source according to claim 1, further comprising a filter arranged at the position of the X-ray transmission window to attenuate a Kβ ray contained in the characteristic X-ray emitted from the secondary target while transmitting and emitting a Kα ray also contained in the same characteristic X-ray.

3. An X-ray source comprising:
   a vacuum container having an X-ray transmission window;
   an electron gun which generates annular electron beam within the vacuum container;
   an annularly-shaped primary target having an angled inner surface and positioned within the vacuum container and entered by the annular electron beam from the electron gun to emit an X-ray; and
   an unshielded secondary target arranged in opposed relation to the primary target and being surrounded by the primary target and positioned at a center of the primary target within the vacuum container,
   wherein the secondary target configured with an outer surface that is parallel to the angled inner surface of the primary target, so that a characteristic X-ray generated by the secondary target, due to the excitation of the X-ray emitted from the primary target, is emitted toward the X-ray transmission window.

4. The X-ray source according to claim 3, further comprising a filter arranged at the position of the X-ray transmission window to attenuate a Kβ ray contained in the characteristic X-ray emitted from the secondary target while transmitting and emitting a Kα ray also contained in the same characteristic X-ray.

5. An X-ray source comprising:
   an electron gun which generates an electron beam;
   a primary target, entered by the electron beam from the electron gun, and configured to transmit and emit an X-ray; and
   a secondary target unit having a plurality of secondary targets arranged to about against the primary target and movable with respect to a position of X-ray generation of the primary target,
   wherein the secondary targets arranged at the position of X-ray generation and configured transmit and emit a characteristic X-ray, due to the due to the excitation of the x-ray emitted from the primary targets.

6. The X-ray source according to claim 5, further comprising a filter unit having a plurality of filters movable with respect to the position of X-ray generation, wherein the filters arranged at the position of X-ray generation attenuate a Kβ ray contained in the characteristic X-ray emitted from the secondary targets while transmitting and emitting a Kα ray also contained in the same characteristic X-ray.

* * * * *